(12) United States Patent
Connaris et al.

(10) Patent No.: US 9,066,894 B2
(45) Date of Patent: Jun. 30, 2015

(54) CARBOHYDRATE BINDING MOLECULES

(75) Inventors: Helen Connaris, St. Andrews (GB); Garry Taylor, St. Andrews (GB)

(73) Assignee: UNIVERSITY COURT OF THE UNIVERSITY OF ST. ANDREWS, St. Andrews (GB)

( * ) Notice: Subject to any disclaimer, the term of this patent is extended or adjusted under 35 U.S.C. 154(b) by 660 days.

(21) Appl. No.: 13/063,537

(22) PCT Filed: Sep. 11, 2009

(86) PCT No.: PCT/GB2009/002189
§ 371 (c)(1), (2), (4) Date: May 31, 2011

(87) PCT Pub. No.: WO2010/029312
PCT Pub. Date: Mar. 18, 2010

(65) Prior Publication Data
US 2011/0269670 A1  Nov. 3, 2011

Related U.S. Application Data

(60) Provisional application No. 61/096,569, filed on Sep. 12, 2008.

(51) Int. Cl.
*A01N 37/18* (2006.01)
*A61K 38/04* (2006.01)
*C12N 5/00* (2006.01)
*A61K 31/00* (2006.01)
*A61K 31/74* (2006.01)
*G01N 33/569* (2006.01)

(52) U.S. Cl.
CPC ............... *A61K 31/00* (2013.01); *A61K 31/74* (2013.01); *G01N 33/56911* (2013.01); *G01N 33/56983* (2013.01); *G01N 2333/11* (2013.01); *G01N 2333/115* (2013.01); *G01N 2333/21* (2013.01); *G01N 2333/285* (2013.01); *G01N 2333/315* (2013.01); *G01N 2400/00* (2013.01); *G01N 2500/02* (2013.01)

(58) Field of Classification Search
None
See application file for complete search history.

(56) References Cited

U.S. PATENT DOCUMENTS

| 5,747,040 | A | 5/1998 | Heerze et al. |
| 5,958,673 | A | 9/1999 | LaClair |
| 2002/0054880 | A1 | 5/2002 | Heerze et al. |
| 2002/0098204 | A1* | 7/2002 | Buchta et al. ............. 424/247.1 |
| 2005/0257905 | A1 | 11/2005 | Shoeseyov |
| 2007/0190163 | A1* | 8/2007 | Malaknov et al. ........... 424/499 |
| 2009/0042793 | A1 | 2/2009 | Balzarini |

FOREIGN PATENT DOCUMENTS

| WO | WO 01/34091 A2 | 5/2001 |
| WO | WO 2004031379 | 4/2004 |

OTHER PUBLICATIONS

International Preliminary Report on Patentability for International Application No. PCT/GB2009/002189 issued Mar. 15, 2011, 6 pages.
Boraston, A. et al., "Carbohydrate-Protein Interactions: Carbohydrate-Binding Modules," Comprehensive Glycoscience, 2007, 3, 661-696.
Boraston, A. et al., "Carbohydrate Recognition by a Large Sialidase Toxin from *Clostridium perfringens*," Biochemistry, 2007, 46 (40), 11352-11360.
Dong, Y. et al., "Advance in the Research of Polyvalent Drugs," Chinese Journal of New Drugs, 2007, 16 (24), 2012-2016.

* cited by examiner

*Primary Examiner* — Marcela M Cordero Garcia
(74) *Attorney, Agent, or Firm* — Hoxie & Associates LLC

(57) ABSTRACT

The present invention provides compounds, compositions, medicaments and methods comprising or using carbohydrate binding molecules. More specifically, the invention provides a means of treating diseases and/or conditions caused or contributed to by pathogens, particularly microbial pathogens and methods of screening, identifying, detecting tagging and/or labelling carbohydrates.

44 Claims, 12 Drawing Sheets a)

Figure 1A:

Titer
512,000    X31 (Stock 1:4000)
           1CBM (285µM)
0.48µM     2CBM (250µM)
0.122µM    3CBM (15.6µM)
           1h, RT b)

30 min, RT 2.5days, 4°C

1CBM (71.25µM, fixed concentration) with titrated vaccine (1:4000 stock), versus titrated vaccine only.

US 9,066,894 B2

CARBOHYDRATE BINDING MOLECULES

CROSS REFERENCE TO RELATED APPLICATIONS

This application is a United States National Stage Application under 35 USC §371 of PCT/GB2009/002189, which claims priority to U.S. Provisional Application No. 61/096,569, filed Sep. 12, 2008, the contents of each of which are incorporated herein by reference.

SEQUENCE LISTING

The instant application contains a Sequence Listing which has been submitted in ASCII format via EFS-Web and is hereby incorporated by reference in its entirety. Said ASCII copy, created on May 18, 2015, is named USA-01-US-Sequence-Listing_ST25-05182015.txt and is 3,897 bytes in size.

FIELD OF THE INVENTION

The present invention provides compounds, compositions, medicaments and methods comprising or using carbohydrate binding molecules. More specifically, the invention provides a means of treating diseases and/or conditions caused or contributed to by pathogens, particularly microbial pathogens and methods of screening, identifying, detecting tagging and/or labelling carbohydrates.

BACKGROUND OF THE INVENTION

The surfaces of most mammalian cells are rich in glycoconjugates and many pathogens have exploited the terminal carbohydrate of these glycoconjugates for cell attachment during the initial stages of pathogenesis. By way of example, the viral pathogens influenza and parainfluenza both bind to sialic acid receptors at the mammalian cell surface.

Sialic acid recognition is mediated via lectins or lectin-like molecules and their corresponding receptors (3). In most cases, sialic acid binding lectins, which also include several viral glycoproteins and bacterial toxins (2,4), as well as the mammalian lectin superfamilies such as the siglecs (5) and selectins (6), bind to their receptor with relatively high affinity due to the multivalent nature of these molecules, thus alleviating the low intrinsic affinity that most protein-carbohydrate interactions are associated with (7,8). Generally, association constants ($K_a$) for the binding of monovalent and divalent sialosides by such lectins can reach $10^4 M^{-1}$. However, by virtue of their multivalency, some sialic acid binding lectins can interact with multivalent cell surface glycans to achieve affinities reaching $10^9 M^{-1}$ by an avidity effect. These enhanced affinities have been shown in part to be due to improved structural packing of proteins promoted by ligand binding, associated with favourable binding energetics (9-11). One of the best-studied multivalent lectin-sialic acid interactions is the influenza virus trimeric hemagglutinin, which can achieve affinities up to $10^8 M^{-1}$ compared to around $4 \times 10^2 M^{-1}$ when one, or both of the entities are not in a multivalent state (12).

Sialidases, or neuraminidases, catalyze the hydrolysis of sialic acids from a variety of glycoconjugates and are often modular enzymes, containing accessory modules attached to the catalytic core of the protein. Some of these modules have been identified as carbohydrate binding modules (CBMs). CBMs are found widely in glycoside hydrolases and are discrete, non-catalytic modules that primarily exist to target the parent enzyme to its substrate for efficient hydrolysis by increasing the concentration of the enzyme at the substrate surface (13). The modules can be single, tandem or in multiples within the glycosyl hydrolase architecture. Studies have shown that they can bind to their specific glycans independently when isolated from the parent molecule, and can behave in a cooperative manner when isolated in tandem (14,15). Currently, CBMs are grouped into 52 families based upon primary sequence similarity (http://www.cazy.org/fam/acc_CBM.html). Subtle differences in the structures of CBMs can lead to diverse ligand specificity, which make CBMs an attractive system for elucidating protein-carbohydrate mechanisms.

A poster entitled "Engineering Multivalent Sialic Acid Recognition using the CBM40 module from *Vibrio cholerae* Sialidase" (published 17 May 2008: see http://www.biochem.emory.edu/conferences/glycot/Images/GlycoTProgram-Posters.pdf) describes the development of reagents with increased affinity for sialic acid through multivalency. However, the poster does not disclose that such reagents have any application in the treatment of diseases and/or conditions caused by pathogens.

It is well documented that there is increasing resistance to currently available influenza antivirals (in particular, Roche's Tamiflu) and this has emphasized the need to look at alternative methods to combat influenza. Previous studies have indicated the use of non-toxic lectins, such as SNA lectin from the elderberry as an influenza virus inhibitor but this demonstrated weak binding to sialic acid and required the presence of two or three different sugar moieties for recognition and effective inhibition. Recent work using a recombinant sialidase-fusion protein designated DAS181 (Fludase, developed by NexBio Inc.) is currently being investigated as another of these alternatives. This protein effectively removes sialic acids from the surface of epithelial cells, rendering the virus unable to bind to receptors. However, by removing sialic acids using a sialidase, this can also expose cryptic receptors, which may serve as receptors for other pathogens.

The present invention aims to provide compounds, compositions, medicaments and methods useful in the treatment of diseases and/or conditions caused by pathogens and to obviate the problems associated with the prior art.

SUMMARY OF THE INVENTION

The present invention is based on the finding that carbohydrate-binding molecules (CBMs) may be exploited to combat and/or prevent diseases or conditions, which occur as a result of infection with viral and/or bacterial pathogens.

It is known that in order to bind/adhere, colonise or gain entry into cells, a number of pathogens exploit the presence of carbohydrates on cell surfaces. By way of example, respiratory pathogens such as viruses belonging to the Orthomyxoviridae or Paramyxovirus families utilise cell surface carbohydrates to bind and gain entry to specific cell types in a variety of mammalian tissues. Similarly, bacteria such as those belonging to the *Streptococcus* genus exploit cell surface carbohydrates as a means of binding/adhering to and/or entering certain cells.

The surfaces of mammalian cells comprise numerous different types of molecule. In particular, mammalian cells are rich in glycoconjugates, the terminal carbohydrate of which is typically sialic acid. Accordingly, certain pathogens have evolved to exploit the presence of sialic acid at the cell surface to bind/adhere and/or gain entry to those cells.

Members of the CBM group normally function to target or direct glycosyl hydrolase enzymes such as sialidase or neuraminidase, to their substrates for efficient hydrolosis. As such, CBMs have an affinity for cell surface carbohydrates such as, for example, sialic acid, galactose, fucose, N-acetylglucosamine, and blood group antigens. One of skill in the art will appreciate that a compound which exhibits an affinity for a cell surface carbohydrate, may be used to block a pathogen's ability to bind to, or recognise, that carbohydrate and thus may prevent the pathogen from colonising and/or entering the cell.

Accordingly, the inventors have discovered that by exploiting the CBM's affinity for carbohydrates, it is possible to provide compounds, compositions, medicaments and/or methods useful in the treatment of a range of diseases and/or conditions caused or contributed to by those pathogens which bind/adhere or otherwise associate with cell surface carbohydrates during pathogenesis.

Thus, in a first aspect, the present invention provides a carbohydrate-binding module (CBM) for use in treating or preventing a disease and/or condition caused or contributed to by one or more pathogens.

In a second aspect, the present invention provides the use of a carbohydrate-binding module (CBM) for the manufacture of a medicament for the treatment or prevention of a disease and/or condition caused or contributed to by one or more pathogens.

In addition to the above, a third aspect of this invention provides a pharmaceutical composition comprising a CBM for use in treating or preventing a disease and/or condition caused or contributed to by one or more pathogens.

Preferably, the pharmaceutical compositions provided by this invention are formulated as sterile pharmaceutical compositions and suitable excipients, carriers or diluents may include, for example, water, saline, phosphate buffered saline, dextrose, glycerol, ethanol, ion exchangers, alumina, aluminium stearate, lecithin, serum proteins, such as serum albumin, buffer substances such as phosphates, glycine, sorbic acid, potassium sorbate, partial glyceride mixtures of saturated vegetable fatty acids, water salts or electrolytes, such as protamine sulphate, disodium hydrogen phosphate, potassium hydrogen phosphate, sodium chloride, zinc salts, colloidal silica, magnesium trisilicate, polyvinyl pyrrolidone, cellulose-based substances, polyethylene glycon, sodium carboxymethylcellulose, polyacrylates, waxes, polyethylene-polypropylene-block polymers, polyethylene glycol and wool fat and the like, or combinations thereof.

Said pharmaceutical composition may be formulated, for example, in a form suitable for oral, parenteral or topical administration.

One of skill in the art will appreciate that in addition to the use of individual or single CBMs which bind specific carbohydrates, the compounds, compositions and medicaments provided herein may further comprise other CBMs which either bind to or express an affinity for, an alternate carbohydrate, or which exhibit a different affinity for the same carbohydrate.

As stated, in addition to providing compounds, compositions and/or medicaments for use in treating or preventing a variety of diseases and or conditions, the present invention also provides methods useful in the treatment of subjects, particularly human subjects, suffering from, or at risk of contracting, a disease and/or condition caused or contributed to by a pathogen, particularly those pathogens which are capable of binding cell surface carbohydrates.

Accordingly, a fourth aspect of this invention provides a method of treating or preventing a disease caused or contributed to by a pathogen, said method comprising the step of administering a therapeutically effective amount of a carbohydrate binding module (CBM).

The present invention represents a distinct advantage over existing treatments for diseases and/or conditions caused or contributed to by pathogens (for example viral and/or bacterial respiratory pathogens) which involve, for example, the enzymatic removal of cell surface carbohydrates. Strategies of this type may expose cryptic receptors to other pathogens rendering the cells vulnerable to infection. By blocking access to cell surface carbohydrates rather than removing them from the cell surface, this problem is avoided and furthermore, since the CBMs described herein bind to terminal carbohydrate residues (such as, for example sialic acid), the CBM might not elicit an immune response.

The term "pathogen" as used herein, should be understood as encompassing any pathogen which is capable of binding, recognising or otherwise associating with a cell surface carbohydrate and particularly those which have evolved to exploit or utilise the presence of cell surface carbohydrates as a means of binding/adhering to and/or entering a cell. As such, in one embodiment, the term "pathogen" encompasses microbial pathogens and includes respiratory pathogens such as viruses belonging to the Orthomyxoviridae or Paramyxoviridae families, for example influenza and human parainfluenza, as well as bacteria belonging to the *Streptococcus* genus such as *Streptococcus pneumoniae* and/or *Hemophilus influenzae, Pseudomonas aeruginosa*—all of which are capable of binding carbohydrates on the surface of mammalian cells. One of skill will appreciate that the mammalian cell most frequently colonised/infected by pathogens of the type described herein, are epithelial cells, especially those lining the mucosal tracts (for example, respiratory epithelial cells).

In view of the above, the diseases and/or conditions treatable or preventable using the compounds, compositions, medicaments or methods provided herein are many and varied and should be considered as those which are caused or contributed to by any of the pathogens mentioned herein. Accordingly, diseases and/or conditions caused or contributed to by viral respiratory pathogens such as, for example Influenza and/or Parainfluenza and bacterial pathogens such as, for example, *Streptococcus pneumoniae*, may benefit from the use of the various compounds, compositions, medicaments and/or methods provided herein. In this regard, the present invention provides compounds, compositions, medicaments and/or methods for use in treating and/or preventing diseases or conditions such as influenza and viral and/or bacterial respiratory diseases such as croup, pneumonia and bronchitis. In view of the above, one embodiment of the present invention provides compounds, compositions, medicaments and/or methods for use in treating diseases caused or contributed to by one or more pathogens selected from the group consisting of Influenza virus; Parainfluenza virus; and *Streptococcus pneumoniae*.

The term "carbohydrate" should be understood to encompass any carbohydrates especially those present at the cell surface and in particular those present on the surface of mammalian cells, such as mammalian epithelial cells. It should also be understood that while the term "carbohydrate" may encompass monosaccharide units, it may also encompass polysaccharides, glycan chains and or the carbohydrate moiety of a glycoconjugate. As such, the term "carbohydrate" may include, for example, the sialic acids, a family of carbohydrates having a nine-carbon backbone and which are located at the terminal (or distal) end of glycan chains at the cell surface. The sialic acid family encompasses a number (approximately 50) of derivatives that may result from acetylation, glycolylation, lactonization and methylation at C4, C5, C7, C8 and C9. Furthermore, sialic acids are found linked α(2,3) or α(2,6) to Gal and GalNAc or α(2,8) or α(2,9) to another sialic acid. Accordingly, it is important to understand that while the term "sialic acid" is used throughout this specification, it should be understood as encompassing all derivatives, analogues or variants (either naturally occurring or synthetically generated) thereof as well as dimers, trimers, oligomers, polymers or concatamers comprising the same. Other cell surface carbohydrates could include N-acetylglucosamine, galactose, N-acetylgalactosamine, fucose, mannose, and their complexes found in such epitopes as blood group antigens.

CBMs are found widely in nature and exhibit a wide range of affinities for a variety of different carbohydrates. To date, the CBMs have been grouped into 52 families based on primary sequence similarity and it should be understood that the invention may concern any CBM. Of course, in order to treat a disease or condition known to be caused by a pathogen, which binds to a particular cell surface carbohydrate, a CBM which binds to or exhibits an affinity for that carbohydrate, will be particularly useful in the treatment or prevention of that disease or condition.

One embodiment of the invention concerns those CBM molecules, which exhibit an affinity for or bind to sialic acid. One of skill will appreciate that CBMs which bind to or exhibit an affinity for sialic acid, will be useful as compounds or in compositions, medicaments or methods for treating diseases and/or conditions caused or contributed to by pathogens which bind or otherwise associate with sialic acid during pathogenesis.

It should be noted that a number of different CBMs may exhibit an affinity for a particular carbohydrate and the magnitude of that affinity may vary. Nevertheless, it should be understood that in the case of CBMs which bind cell surface carbohydrates such as sialic acid, any CBM exhibiting an affinity for sialic acid should be considered as potentially useful.

Among those potentially useful CBMs are those which belong to family 40 and which may otherwise be known as the "CBM40" CBMs. Included within the CBM40 family are CBMs derived from *Vibrio cholerae* and *Clostridium perfringens*.

The CBM40 derived from *V. cholerae* exhibits a relatively high affinity ($K_d$~30 µM) for sialic acid whereas the CBM40 derived from *C. perfringens* exhibits a high millimolar affinity towards sialic acid.

In addition to the above, the inventors have discovered that while a single CBM molecule may exhibit an affinity for a particular carbohydrate (such as, for example, sialic acid), by linking or combining together two or more CBM molecules, it is possible, through avidity, to generate a molecule having a higher affinity for that carbohydrate.

Thus, this invention also concerns multivalent CBM molecules or polypeptides referred to hereinafter as "CBM polymers", which comprise one or more CBMs (or monomers) joined, linked or conjugated together by some means.

Accordingly, a fifth aspect of this invention provides a CBM polymer comprising two or more CBMs (CBM monomers).

The term "polymer" will be readily understood by one of skill in this field to encompass molecules comprising a number of linked units. In this regard, the term "CBM polymer" may be used to describe CBM-dimers (i.e. two CBM monomers), CBM-trimers (three CBM monomers), CBM-tetramers (four CBM monomers) and larger, CBM-oligomers (five or more CBM monomers).

One of skill in the art will appreciate that although it may be desirable to generate CBM polymers comprising identical repeating CBM monomers (for example repeating *V. cholerae* derived CBM40 monomers), it may also be possible to create CBM polymers which comprise a number of different CBM monomers, each being capable of binding a different carbohydrate and/or each exhibiting a different affinity for a particular carbohydrate. Similarly, CBM polymers, which comprise CBM monomers binding, or exhibiting an affinity for, different cell surface carbohydrates are also within the scope of his invention. As such, a CBM polymer according to this invention may comprise CBM monomers having affinity for sialic acid and CBM monomers having affinity for or binding to some other carbohydrate, for example mannose, galactose, fucose, N-acetylglucosamine.

As stated, by joining, linking or conjugating together CBM monomers, it is possible to create a larger polymeric molecule, which, through avidity, exhibits a greater affinity for a particular carbohydrate or for a number of carbohydrates. Thus, while a particular CBM monomer, for example the CBM40 derived from *V. cholerae* may exhibit affinity for sialic acid, when two or more of said CBM40 monomers are linked, joined or conjugated together, the resulting polymer may exhibit an increased affinity for sialic acid.

Accordingly, the invention and in particular the term "CBM" as used in the first, second and third and fourth aspects of this invention, should be understood as including the CBM polymers described herein.

One of skill in the art will appreciate that a CBM polymer comprising CBM monomers, which bind to or have affinity for different carbohydrates, may itself bind to or exhibit an affinity for the same carbohydrates. For example, if a CBM polymer comprises CBM monomers which bind to or have affinity for two different cell surface carbohydrates, the resulting CBM polymer may also bind to or exhibit an affinity for the same two cell surface carbohydrates.

CBM polymers which comprise a number of different CBM monomers and consequently bind to or exhibit an affinity toward a number of different carbohydrate molecules, may be particularly useful in compositions, compounds, medicaments and/or methods to treat or prevent diseases and/or conditions caused or contributed to by more than one pathogen.

For example, where a subject suffers from or is predisposed to contracting at least two diseases or conditions caused or contributed to by two different pathogens each of which binds a different cell surface carbohydrate (as a means of colonising and/or entering cells) a CBM polymer comprising CBM monomers which recognise, bind or otherwise associate with these carbohydrates may be useful in the treatment or prevention of said diseases and/or conditions. Alternatively, diseases and/or conditions caused by two or more pathogens may be treated using compounds or compositions, medicaments or methods utilising the relevant monomeric CBMs.

One of skill will appreciate that there are many ways in which amino acids, proteins and/or peptides can be linked together. In one embodiment, amino acids, peptides and/or proteins may be joined linked or conjugated by chemical means and/or via cloning and/or PCR technology.

By way of example, the nucleotide sequence encoding the relevant CBM(s) may be amplified by PCR and modified such that one or more copies of the same can be ligated together or to other CBM encoding nucleotide sequences. In addition, the CBM nucleotide sequences may be further modified to include at their 3' and/or 5' ends sequences encoding linker moieties comprising one or more amino acid residues.

CBM polymers (or multivalent CBMs) may also be generated using CBM monomers modified to include, for example, oligomerisation domains. Molecules possessing such domains may self assemble to form oligomeric structures. In one embodiment the oligomerisation domain may be derived from, for example bacterial species such as *Pseudomonas aeruginosa* which is known to encode a trimerisation domain. PCR based techniques may be used to modify CBM molecules in this way.

The amplified and optionally modified/ligated CBM sequences may then be cloned into suitable vectors for expression and purification of the resulting CBM or CBM polymer. Recombinant CBM monomers (such as those encoding oligomerisation domains) or CBM polymers, may be expressed in, for example, *E. coli*.

In view of the above, a sixth aspect of this invention may provide a method of generating a CBM polymer, said method comprising the step of:
(a) ligating CBM encoding nucleotide sequences; and
(b) expressing the ligated CBM nucleotide sequences to generate a CBM polymer.

As stated, the CBM polymers provided by this invention may comprise CBM monomers linked by some form of linker moiety, which may take the form of one or more amino acids. Although the precise number of amino acids comprising the linker moiety may vary, typically, the linker moiety will comprise any length from 1 to about 30 amino acids.

An alternative means of generating a CBM polymer is to link, through molecular biological techniques, an oligomerisation domain to the CBM. For example, the trimerisation domain found in the pseudaminidase of *Pseudomonas aeruginosa* (residues 335 to 438, Xu, G., Ryan, C., Kiefel, M. J., Wilson, J. C. and Taylor, G. L. (2009) J. Mol. Biol. 386(3), 828-840) could be linked via a linker peptide to one or more CBM(s). Expression of a single construct would then generate a trimer with increased affinity through an avidity effect. Similarly, the tetramerisation domain from the human vasodilator-stimulated phosphoprotein (Kuhnel K., et al. PNAS 2004, 101, 17027-17032), a 45-residue peptide which forms a tetrameric coiled-coil structure could be linked, via a suitable linker, to one or more CBM(s), to form, for example, a tetrameric oligomer with increased affinity through an avidity effect.

A seventh aspect of this invention provides a method of screening for or identifying CBMs potentially useful in the treatment of diseases and/or conditions, said method comprising the steps of:
(i) contacting a CBM or CBM polymer with a cell in the presence of a pathogen known to bind or infect said cell;
(ii) identifying those cells to which the pathogen has bound or which the pathogen has infected; and
(iii) comparing the results with a standard or control assay in which no CBM or CBM polymer has been added;
wherein a decrease in the number of cells to which the pathogen has bound or a decrease in the number of cells infected by the pathogen relative to the control assay, indicates a CBM or CBM polymer potentially useful in the treatment of a disease and/or condition caused or contributed to by that pathogen.

The cell contacted with the CBM/CBM polymer may take the form of a cell monolayer cultured under tissue culture conditions or a tissue biopsy or scraping obtained from a subject. In addition, the cell may be present in an animal, such as a rodent (mouse, rat, guinea pig, rabbit or the like). Where an animal is used in the methods provided by the seventh aspect of this invention, the animal may be administered the CBM or CBM polymer to be tested and simultaneously (or before or after) infected with a pathogen (for example a respiratory pathogen). Furthermore, the standard or control assay may take the form of an animal, which has been infected with a pathogen but not administered the CBM or CBM polymer.

When using animals, in order to determine whether or not a CBM or CBM polymer is potentially useful in the treatment or prevention of a disease caused or contributed to by a particular pathogen, after completion of the method provided by the seventh aspect, cells may be derived from the animal and examined to determine whether or not the pathogen has bound thereto or infected the cells. Additionally or alternatively, the animal may be observed for signs or symptoms of disease. When compared to an animal subjected to the control or standard protocol, a reduction in the severity of the symptoms may indicate that the CBM or CBM polymer administered to that animal might be useful in the treatment of diseases and or conditions caused or contributed to by that pathogen.

In addition to the above, the inventors have discovered that the differential binding capabilities of the various CBMs and CBM polymers described herein, can be exploited to provide a means of screening, identifying, detecting, labelling and/or tagging carbohydrates.

Thus, in an eighth aspect, the present invention provides a method of screening, identifying, detecting, labelling and/or tagging a carbohydrate in a sample, said method comprising the step of:
(a) contacting a sample with a CBM or CBM polymer as described herein, under conditions suitable to permit binding between the CBM/CBM polymer and the carbohydrate(s) it/they bind or have affinity for;
(b) removing unbound CBM or CBM polymer; and
(c) detecting bound CBM or CBM polymer.

One of skill in the art will appreciate that since CBMs exhibit a degree of specificity for certain carbohydrates, the CBM or CBM polymer detected in step (c) will serve as an indication of the carbohydrates present in the sample.

It should be understood that the term "sample" encompasses biological samples such as bodily fluids (urine, blood, plasma, serum, sweat, saliva, semen and the like) as well as samples derived from other sources such as, for example, food, beverages and water sources (rivers, oceans). Indeed, almost any sample thought to contain carbohydrates and to which CBM or CBM polymer can be added, may be used.

In one embodiment, the sample comprises cells, preferably mammalian cells, derived from a tissue biopsy, scraping or secretion. In this way, the method provided by the eighth aspect of this invention may be used to detect the presence of certain cells in a sample. One of skill in this field will readily understand that because cells express a range of carbohydrates at their surface, by contacting a sample with a CBM specific to a carbohydrate known to be expressed on a certain cell type and detecting whether or not the CBM has bound to any cell in the sample, it may be possible to identify the presence of certain cells within a heterogeneous cell population. Techniques such as FACS may be used to identify cells labelled or tagged with CBMs or CBM polymers (optionally modified to include a detectable tag) according to this invention. In addition techniques of this type may be useful for diagnosing diseases or other conditions. For example, CBMs or CBM polymers which bind to or have affinity for carbohydrates known to be expressed on cancerous cells may be used to identify or detect the presence of cancerous cells in a sample.

In order to remove unbound CBM or CBM polymer, the sample::CBM/CBM polymer complexes resulting from step (a) above may be subjected to one or more wash steps with an appropriate buffer.

In one embodiment, the sample may be immobilised on a suitable substrate such as, for example, plastic, glass, agarose, nitrocellulose, paper or the like.

One of skill in the art will appreciate that the CBMs or CBM polymers provided by this invention may be further modified to include one or more detectable tags or labels. In this way, modifying, or conjugating the CBM, or CBM polymer to include an enzyme capable of reporting a level via a colormetric chemiluminescent reaction may achieve the detection of bound CBM or CBM polymer. Such enzymes may include but are not limited to Horse Radish Peroxidase (HRP) and Alkaline Phosphatase (AlkP). Additionally, or alternatively, the CBM or CBM polymers provided herein may be conjugated to a fluorescent molecule such as, for example a GFP and fluorophore, such as FITC, rhodamine or Texas Red. Other types of molecule, which may be conjugated to the CBM or CBM polymers described herein, may include radiolabelled moieties.

In a further embodiment, the CBM polymers or CBMs provided by this invention may be further modified to include a moiety, for example an antibody, a small organic molecule a nucleic acid, drug or toxin, to be delivered to a cell. By identifying those carbohydrates expressed at a cell surface, a CBM or CBM polymer, which binds to or has affinity for one or more of the identified carbohydrates, may be used to deliver a moiety of the type listed above, to that cell.

DETAILED DESCRIPTION

The present invention will now be described in detail with reference to the following Figures, which show:

FIG. 1: (A) Schematic drawing of the *Vibrio cholerae* sialidase showing the central catalytic domain flanked by the lectin-like carbohydrate-binding modules (CBMs). The sialic acid recognizing CBM, CBM40, is on the right. (B) Schematic view of the constructs made in this study.

Figure 2:
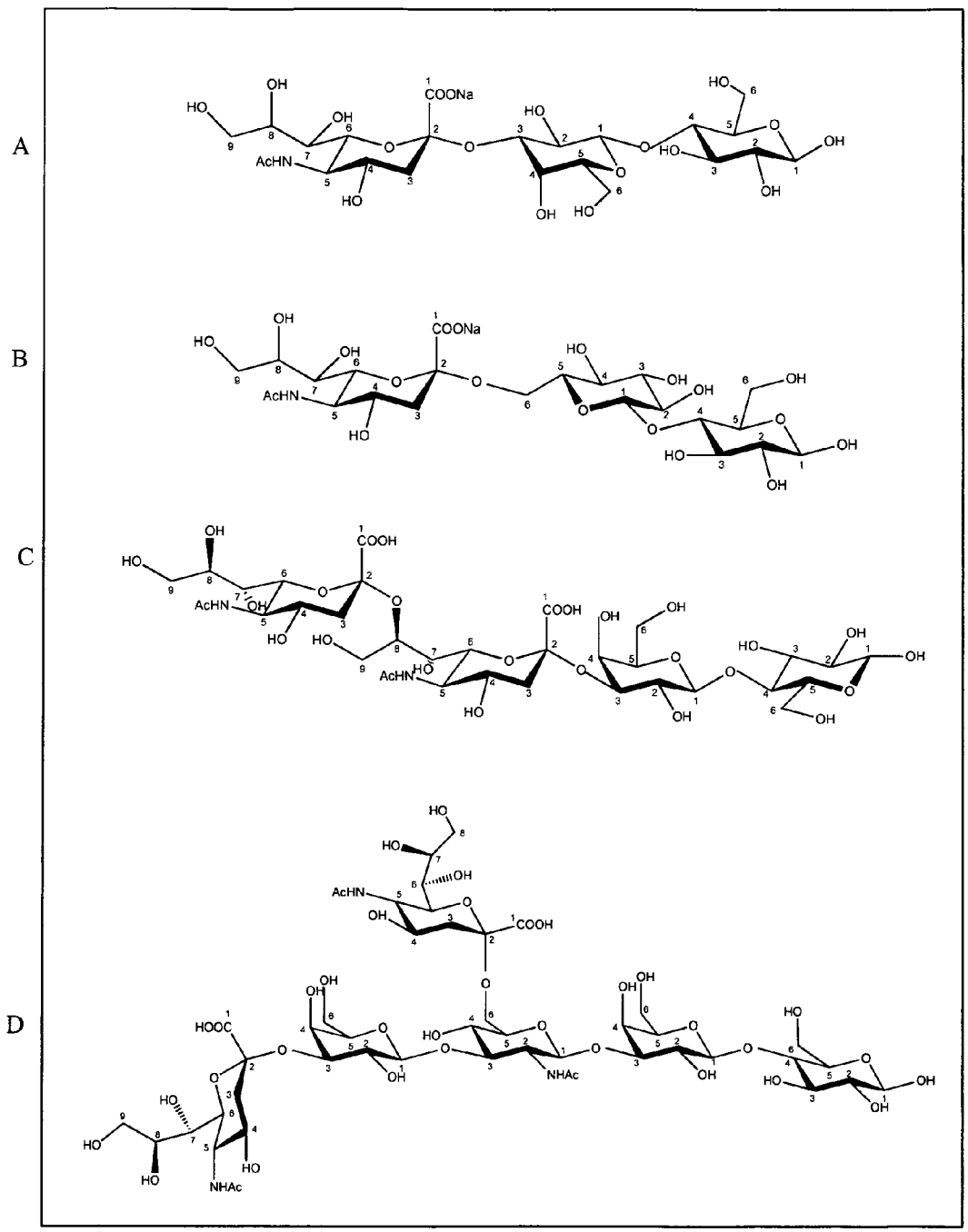

FIG. 2: Sialosides used in the ITC study. (A) 3'sialyllactose, (B) 6'sialyllactose, (C) disialyllactose (DSL), (D) disialyl-lacto-N-tetraose (DSLNT).

FIG. 3: Crystal structure of *V. cholerae* CBM40 in complex with 3'sialyllactose. (A) Interactions of the ligand with the CBM with hydrogen-bonds drawn as dashed lines. The sigma-a weighted Fo-Fc electron density map is drawn at 3σ. (B) The relationship between the three CBM40 modules in the asymmetric unit of the crystal.

Figure 4:
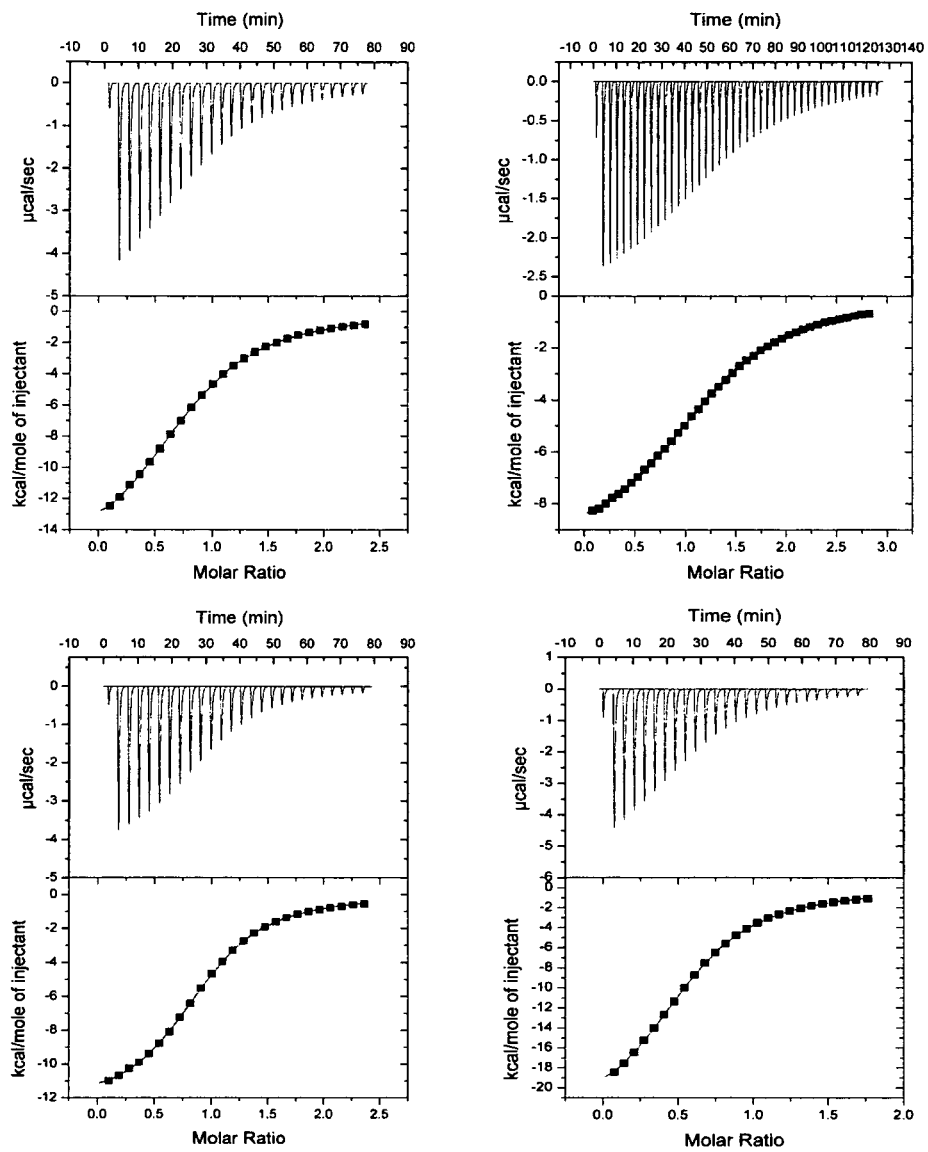

FIG. 4: Isothermal titration calorimetry isotherms showing the binding of various ligands to the isolated CBM40. (A) 3'SL, (B) 6'SL, (C) DSL, (D) DSLNT.

Figure 5:
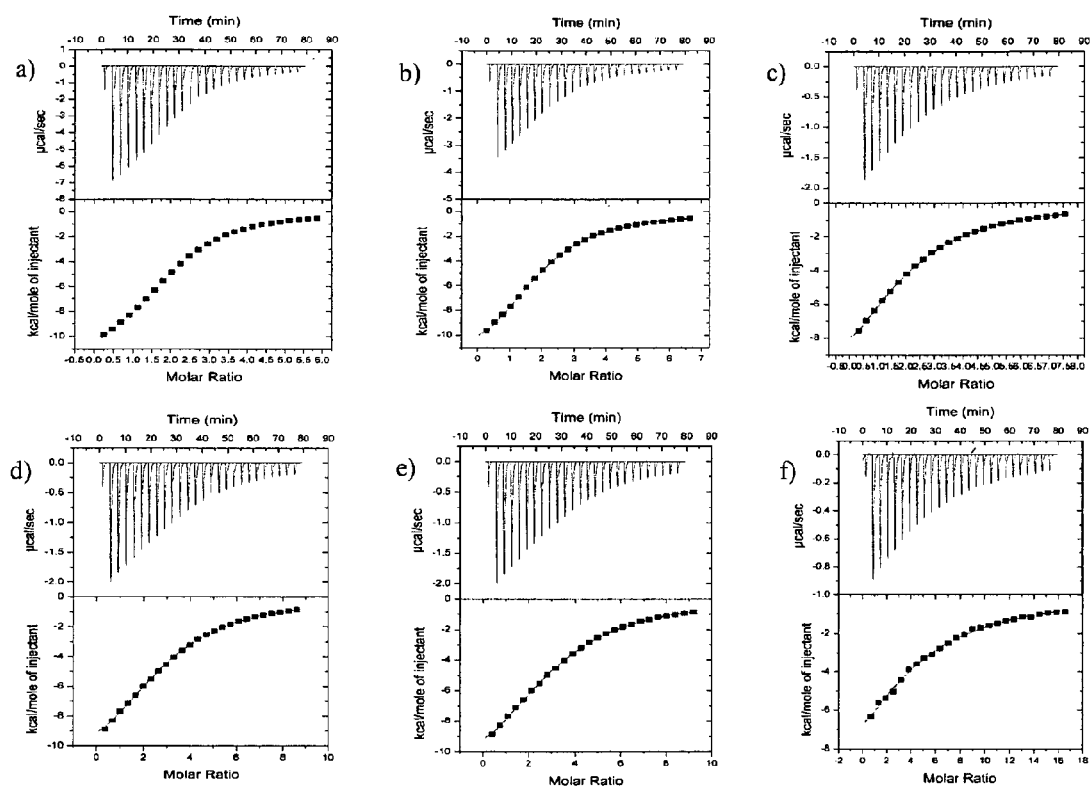

FIG. 5: Isothermal titration calorimetry isotherms showing the binding of 3'SL to various CBM40 constructs. (A) 2CBM (5), (B) 2CBM(10), (C) 2CBM(15), (D) 3CBM(5), (E) 3CBM(10), (F) 4CBM(5).

Figure 6:
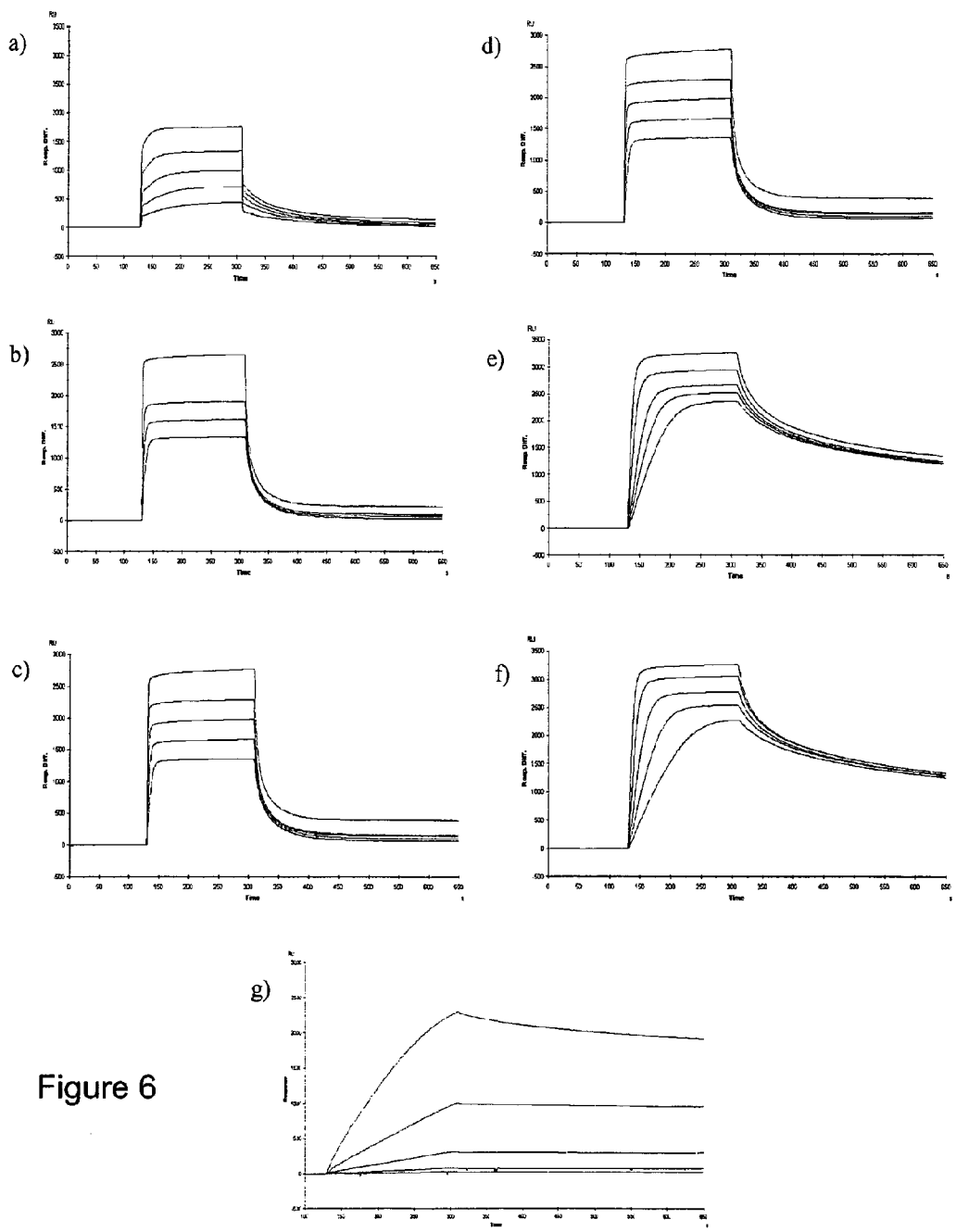

FIG. 6: Surface plasmon resonance (SPR) sensorgrams showing the binding of the CBM40 modules to immobilised 3'sialyllactose receptors. (A) 1CBM, (B) 2CBM(5), (C) 2CBM(10), (D) 2CBM(15), (E) 3CBM(5), (F) 3CBM(10), (G) 4CBM(5).

Figure 7:
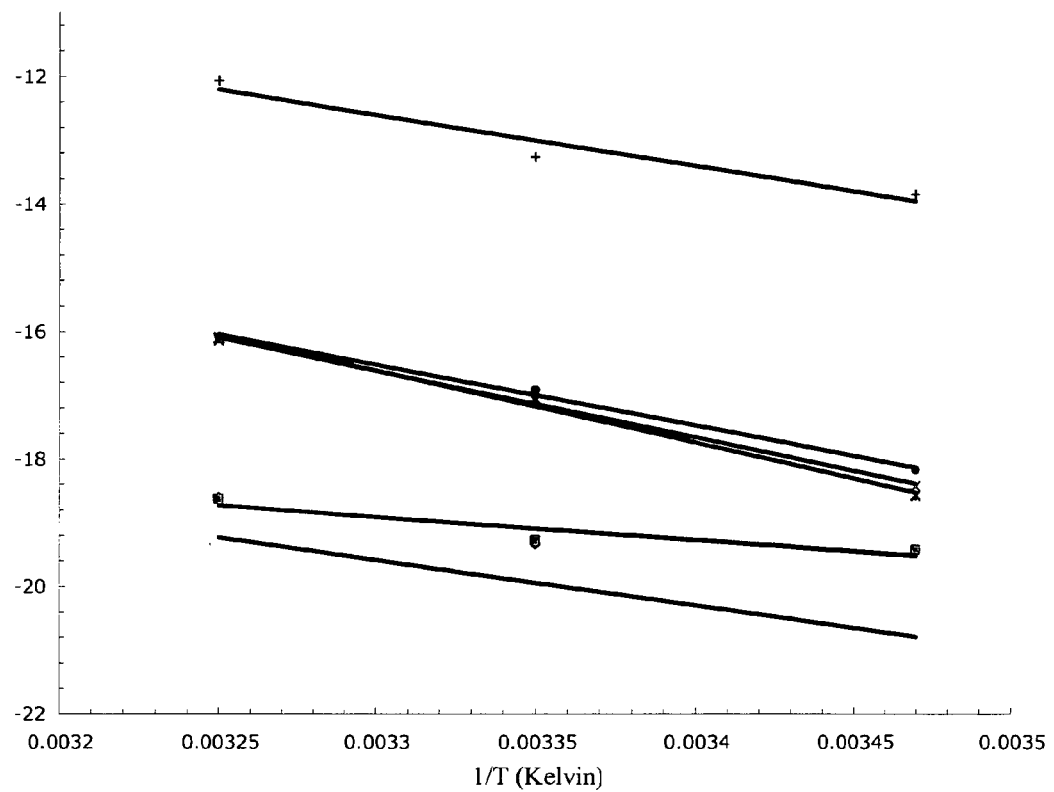

FIG. 7: Van't Hoff plot derived from the SPR experiments at different temperatures.

Figure 8:
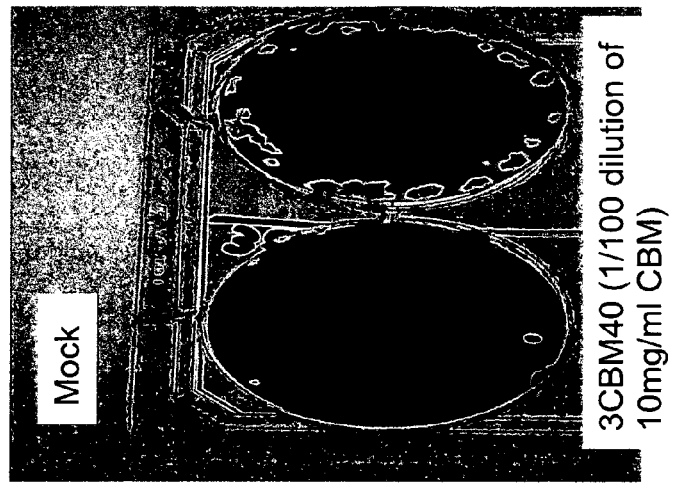
Figure 8:
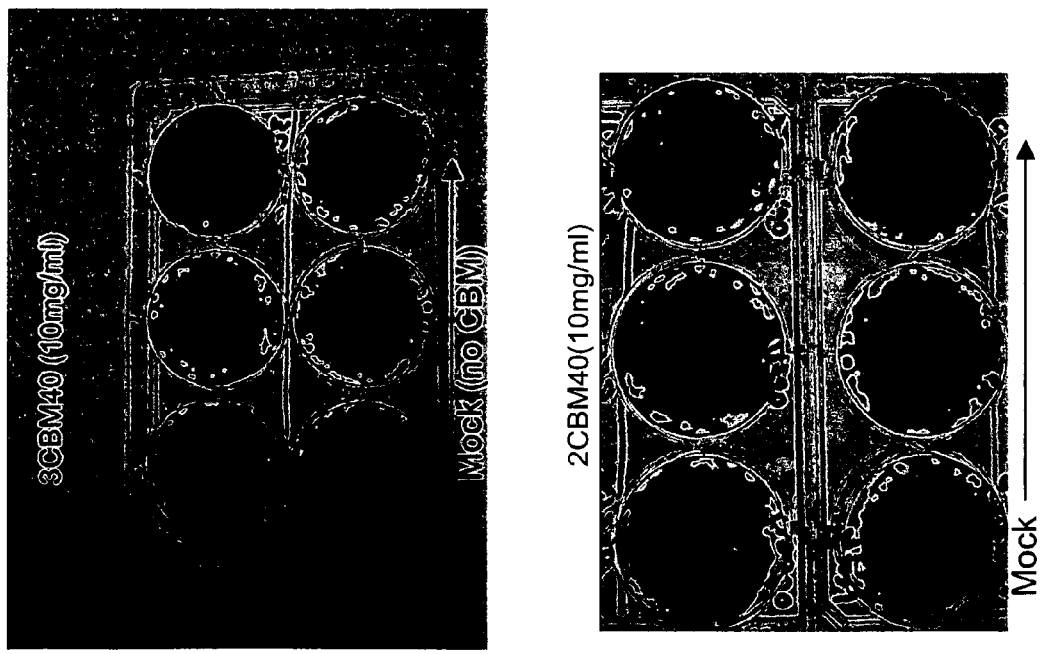

FIG. 8: Plaque assay demonstrating that multivalent CBM40 polypeptides can reduce the binding of influenza virus in vitro.

Figure 9:
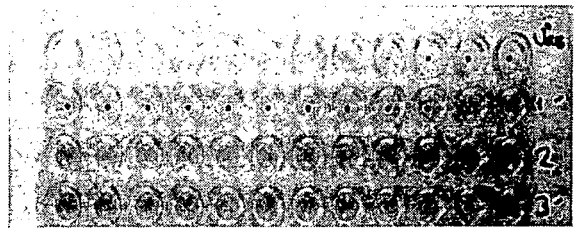
Figure 9:
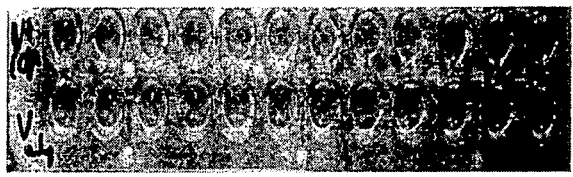
Figure 9:
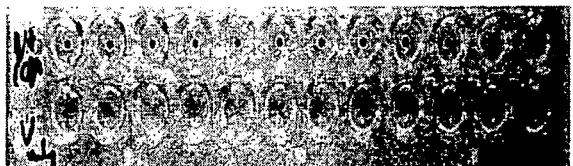

FIG. 9: Hemagglutination assay of chicken red blood cells with (a) vaccine X31, monomeric and multivalent CBM40, and (b) with and without the presence of influenza A virus from vaccine strain X31.

Figure 10:
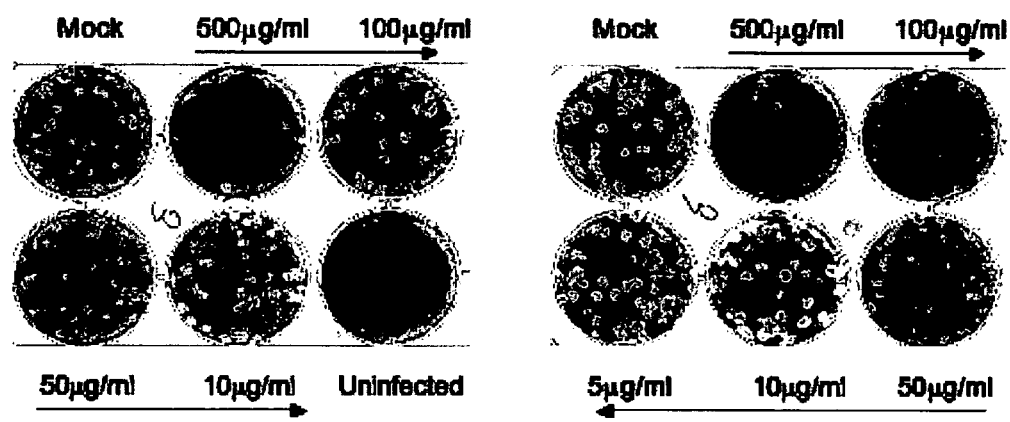
Figure 10:
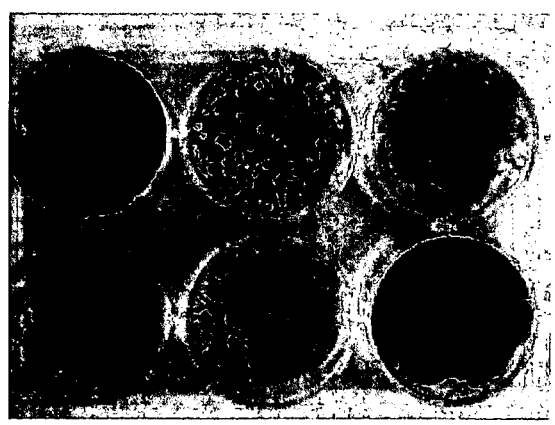

FIG. 10: Mammalian MDCK cell protection by 3CBM(5), 4CBM(5) and CBMTD polypeptides against influenza strain A/Udorn/72 (H3N2).

FIG. 11: (A) GFP-3CBM40 (0.5 mg/ml) binding to cell surface of MDCK cells; (B) Phase contrast micrographs of MDCK cells incubated with GFP-3CBM40, 72 p.i with the Udorn virus. Panel (a) CBM (0.5 mg/ml) only, (b)-(f) 0.5, 0.1, 0.05, 0.01 and 0.005 mg/ml CBM with Udorn virus present, (g) Udorn virus only, and (h) uninfected cells.

Figure 12:
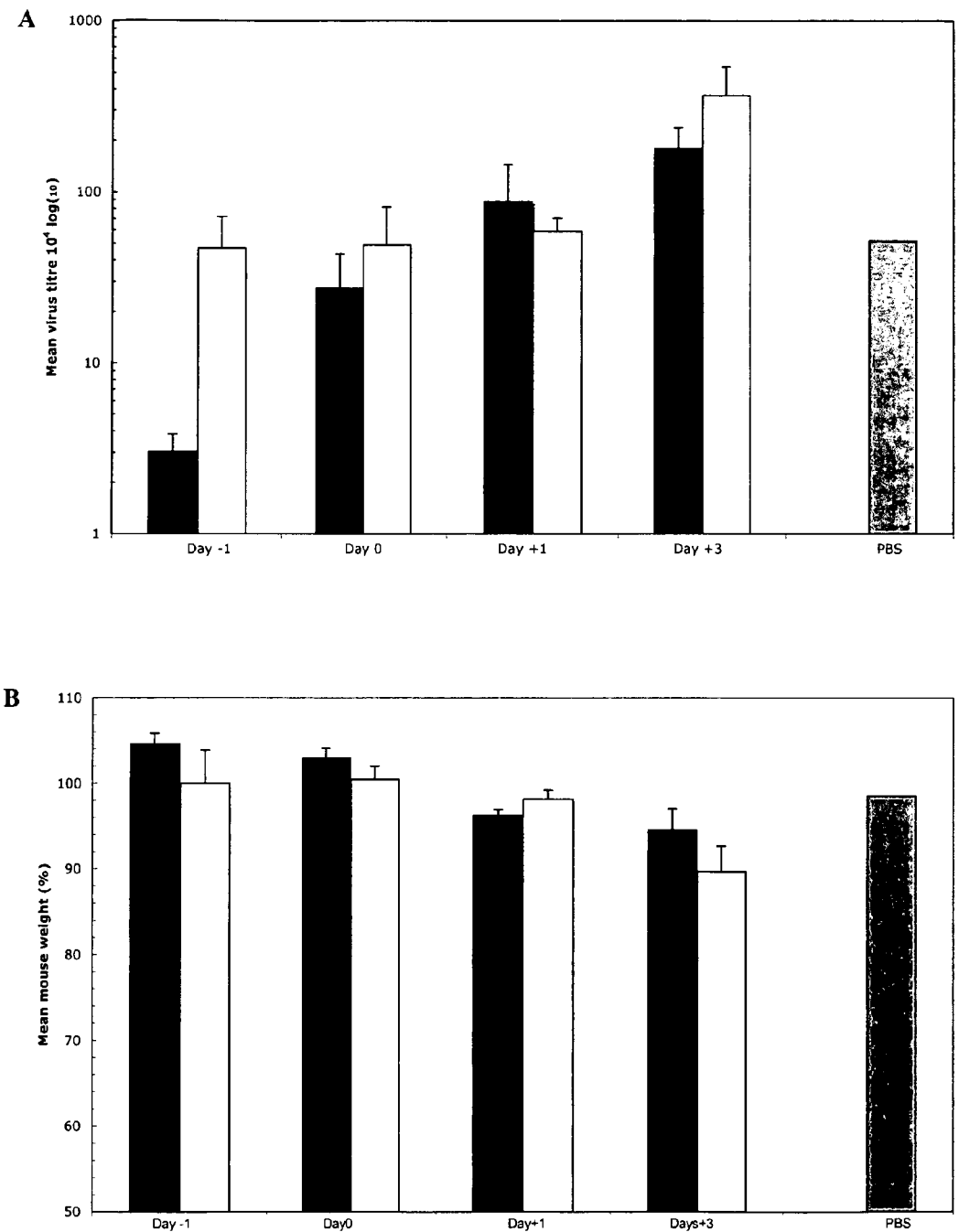

FIG. 12: Effect of 3CBM40 on lung virus titre (A), and mouse weights (B) in influenza A virus infected BALB/c mice. Mice were administered with 3CBM40 (black bars) or with BSA (white bars) 1 day before, on the day, or 1 or 3 days after H1N1 infection ($10^3$ virus pfu). Data were collected from 4 mice per group at 6 days p.i. The virus control group (Day 0) is indicated as PBS on the bar charts.

MATERIALS AND METHODS

Recombinant DNA Techniques

The DNA fragment encoding the family 40 CBM of *V. cholerae* sialidase/neuraminidase (VCNA), residues 25-216, was amplified by PCR from the construct pET30b+ containing the nanH gene (16) using oligonucleotide primer pair 1F and 1R based on the sequence outline in Table 2. The amplified DNA fragment of 573 bp was digested with Nco I and Xho I and cloned into the pEHISTEV vector (an engineered variant of pET30 with an N-terminal 6× His tag that is cleaved by Tobacco Etch Virus (TEV) protease) (Dr H. Liu, unpublished work), digested with the same enzymes and used to transform *E. coli* DH5a. The construct, p1CBM was verified by DNA sequencing (University of Dundee Sequencing Service, UK).

Figure 1B:
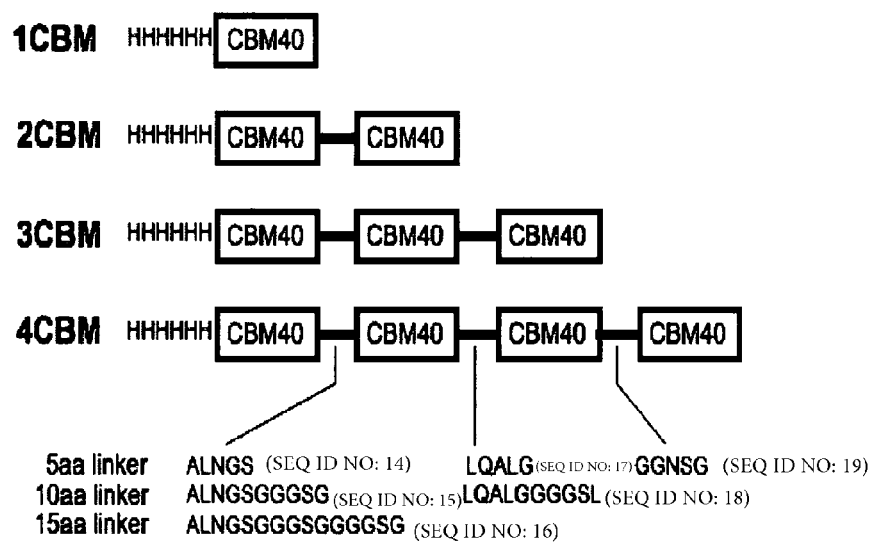

The DNA fragment, encoding the *V. cholerae* CBM40, was modified at the 5'- and 3'-termini to incorporate different restriction endonuclease sites through the use of different primer pairs. This was performed to allow ligation of individual copies of the DNA fragment to generate 2, 3 and 4 copies in tandem (FIG. 1B). Moreover, the primer pairs allowed the insertion of 5, 10 or 15 codons, to represent the length of amino acids linking the individual modules. All these modifications were achieved by PCR amplification using different primer pairs outlined in Table 2, and p1CBM as template. The resulting fragments were cloned into an appropriately digested pEHISTEV vector until the desired number of modules was achieved. These were labelled p2CBM(5), p2CBM(10), p2CBM(15), p3CBM(5), and p3CBM(10), representing 2 and 3 repeating sialic acid-binding domains with the number of amino acids in the linker in parenthesis, respectively. For p4CBM(5), HindIII-EcoRI-modified and EcoRI-XhoI-modified DNA fragments were initially cloned into pET17b digested with the appropriate enzymes before assembling the final gene in pEHISTEV. All constructs were propagated in *E. coli* DH5a. Positive clones were verified by DNA sequencing before transforming expression hosts *E. coli* BL21(DE3) (1CBM, 2CBM(5), 3CBM(5), 3CBM(10), 4CBM(5) and *E. coli* BL21(DE3) Gold (2CBM(10), and 2CBM(15) respectively) for protein production.

Protein Production and Purification

All constructs were grown and expressed as described for VCNA (16). Briefly, 1 L aliquots of Luria-Bertani Broth media containing 30 µg/ml kanamycin, were inoculated with single colonies and grown at 37° C. until the optical density of the culture reached 0.4-0.6 at 600 nm. Cells were subjected to heat shock for 20 min in a 42° C. water bath before being cooled down to 25° C. and induced with 1 mM IPTG, and left to shake overnight at the same temperature. Cells were harvested by centrifugation (8000×g, 4° C.), and pellets frozen at −20° C., until required.

All polypeptides were purified by nickel affinity chromatography as previously described (16). Samples were analysed using SDS PAGE and partially purified polypeptides were dialyzed into TEV protease cleavage buffer (PBS, 0.3M NaCl, 1 mM DTT, 0.5 mM EDTA, 20 mM imidazole) and digested overnight with TEV protease. Each polypeptide was then further dialysed with PBS, 0.3M NaCl, 10 mM imidazole buffer before a second round of purification on a nickel-charged column to remove undigested His-tagged polypeptides. Untagged polypeptide samples were dialysed extensively in 10 mM HEPES buffer, pH 7.4, 0.15M NaCl and concentrated before use.

Crystallisation and Structure Determination

Crystals of the single *V. cholerae* CBM40 were obtained in 0.1M MOPS pH 6.5, 1.1M lithium sulphate, 0.6M ammonium sulphate as precipitant, using the sitting drop method. Crystals were cryoprotected by transferring crystals first into 10% (v/v) glycerol-precipitant mix before leaving in 20% (v/v) glycerol;—precipitant. Diffraction data extending to 2.5 Å were collected on beamline BM-14 of the ESRF. The structure was solved using molecular replacement program PHASER (18) which found three CBM40 monomers in the asymmetric unit. Refinement was carried out using REFMAC (19) with COOT being used for model building (20). Data collection and refinement statistics are shown in Table 3.

Isothermal Titration Calorimetry (ITC)

ITC experiments were performed on a VP-ITC microcalorimeter from Microcal Inc. (Northampton, Mass.) with a cell volume of 1.4 ml. Unless stated otherwise, all ITC titrations were performed at 25° C. in 10 mM HEPES buffer pH7.4, containing 0.15M NaCl. For the characterization of the isolated CBM40 (1CBM), the following ligands were used: 3'sialyllactose (3'SL), 6'sialyllactose, (6'SL), and disialyl-lacto-N-tetraose (DSLNT), purchased from Dextra Labs (Reading, UK) and disialyllactose (DSL) from Sigma-Aldrich, UK (FIG. 2). The lyophilised sialoside ligands were resuspended in degassed, filtered buffer that was used for the dialysis of the peptide construct. For all other polypeptide constructs, 3'sialyllactose was used as the ligand throughout. Protein concentrations were determined at $A_{280}$, using calculated molar extinction coefficients for 1CBM (38410 $M^{-1}$ $cm^{-1}$), 2CBM constructs (75860 $M^{-1}$ $cm^{-1}$), 3CBM constructs (113790 $M^{-1}$ $cm^{-1}$) and 4CBM(5) (151720 $M^{-1}$ $cm^{-1}$), respectively. The concentrations of CBM40 polypeptides were 0.007-0.084 mM and the sialosides were 0.45-2.14 mM. Aliquots of sialosides (10 μl, unless stated otherwise) were titrated into each polypeptide solution. The heats of dilution were subtracted from binding isotherm data before data were fitted by means of a nonlinear regression analysis using a one-binding site model from MicroCal Origin software.

Surface Plasmon Resonance (SPR)

Binding kinetics were determined by SPR using a BIACORE 3000 biosensor instrument (GE Biosystems). Prior to use, a streptavidin coated (SA) biosensor chip was docked into the instrument and preconditioned with three consecutive 1-minute injections of 1M NaCl in 50 mM NaOH. Biotinylated 3'sialyllactose-PAA (Glycotech) was diluted to 1 μg/ml in HBS-P (10 mM HEPES pH 7.4, 0.15M NaCl and 0.005% surfactant P20) before being injected over 3 of the 4 flow cells in the chip. Typical immobilization levels of the ligand for each cell were approximately 500 RU. A reference surface was also prepared for subtraction of bulk effects and non-specific interactions with streptavidin. The running buffer consisted of 10 mM HEPES pH 7.4 at a flow rate of 100 μl/min.

Interaction analysis for each peptide construct with immobilized 3'sialyllactose was performed in running buffer at 15, 25 and 35° C. Purified peptide constructs were diluted into HBS-P to give a series of concentrations for 1CBM, 0.625 μM, 1.25 μM 2.5 μM, 5 μM, 10 μM; 2CBM constructs 20 nM, 125 nM, 250 nM, 500 nM and 1000 nM; 3CBM constructs 1 nM, 5 nM, 20 nM, 62.5 nM and 125 nM, and for 4CBM 0.18 nM, 0.5 nM, 1.6 nM 5 nM and 15 nM. All analytes were injected over the flow cell surface at 30 μl/min. The dissociation of analyte from the surface was achieved in running buffer at the same flow rate for 3-5 min. Surfaces were regenerated with two consecutive 30 s injections of 10 mM glycine-HCl pH 2.5 at 30 μl/min. The affinity, as described by the equilibrium dissociation constant ($K_D$) was determined globally by fitting to the kinetic simultaneous ka/kd model, assuming Langmuir (1:1) binding, using BIAevaluation software (BIAcore).

The free energy change of the interaction of the different CBM polypeptide constructs with biotinylated 3'sialyllactose-PAA was determined by using the equilibrium dissociation constants provided by the ratios of the kinetic rate constants for each temperature. van't Hoff plots of ln $K_D$ versus 1/T yielded values for ΔH/R from the slope and −ΔS/R from the y intercept.

Plaque Assay

A virus plaque assay was used to demonstrate the efficacy of binding multivalent CBM40 polypeptides in the presence of the influenza A virus. Confluent ($10^6$ cells) MDCK monolayers in 6-well plates were washed twice with serum-free DMEM and incubated with either 1 ml solution of 2CBM40, or 3CBM40 (10 mg/ml, 10-fold serially diluted in serum-free DMEM) at 37° C. (+5% $CO_2$) for 1 h. Serum-free DMEM alone was used in parallel 'mock' incubations. CBM40 reagents were then removed and monolayers were inoculated with ~80 PFU of influenza virus A/Udorn/72 [H3N2] for 1 h at 37° C. (+5% CO2). Following virus adsorption, the inoculum was removed and cells were overlayed with 10 mM HEPES (pH 7.4) in DMEM supplemented with 2 μg/ml trypsin and 1% (w/v) agarose. Inverted plates were incubated at 37° C. (+5% CO2) for 2-3 days. Plaques were visualised by fixing the monolayers in 5% formaldehyde and staining with 0.1% crystal violet.

Haemagglutination Assay

Chicken red blood cells in Alsever's solution were spun and washed at least 4 times with PBS. The cells were finally resuspended in 1% (v/v) PBS. The vaccine strain X31 (with cell surface Hong Kong/68 HA and NA), was titrated in 96-well plates using a 2-fold serial dilution of a 1:4000 stock in PBS, to which an equal volume of red blood cells has been added. Plates were incubated at room temperature for at least 30 mins. The endpoint was calculated as the lowest concentration of virus where hemagglutination is observed. CBMs were diluted appropriately and titrated in PBS, to which an equal volume of cells has been added. An endpoint for CBM binding to cells was also calculated. Experiments were then carried out to determine the effect of a fixed concentration of 1CBM with titrated virus versus virus only when incubated with chicken RBCs.

Development of CBM.TD Using an Oligomerisation Domain

The pEHISTEV construct containing 1CBM40, p1CBM, was modified to include an oligomerization domain at the C-terminus to allow the polypeptide to self-assemble into an oligomeric structure, when expressed in *E. coli*. For this, the trimerization domain from *Pseudomonas aeruginosa* pseudominidase was used (Xu et al, 2009). The DNA fragment encoding residues 333-440 was amplified by PCR using primers containing BamHI and XhoI and ligated to p1CNM, previously digested with the same enzymes. This was subsequently transformed into *E. coli* BL21(DE3) Gold cells using conditions similar to the growth and expression of all other CBM40 constructs. The oligomer was purified using nickel affinity, and TEV protease digestion, and presented a molecular weight of approximately 100 kDa after gel filtration (data not shown).

Development of GFP-3CBM40 to Monitor Cell-Surface Bound Sialic Acid by CBM40

For the construction of a GFP-fused 3CBM40 fragment, the 3CBM40 fragment was digested with NcoI-XhoI from p3CBM(5) and inserted into a similarly digested pEHISTEV vector containing the gene encoding the enhanced green fluorescent protein (eGFP) downstream of the N-terminal Histag (Liu et al 2009; Connaris et al, 2009). This construct was tested against MDCK cells to determine whether the CBM40 bound to sialic acid at the cell surface. For this, confluent monolayers of MDCK cells in 96-well plates were incubated for 1 h at 37° C. with different concentrations of GFP-3CBM before the addition of the influenza strain A/Udorn/72 (H3N2) virus (moi=0.002) for a further 1 h at the same temperature. The mixture was removed and DMEM, without FCS, was added and plates were incubated for 72 hr.

Mouse Studies: Dose Finding Experiment:

To evaluate the prophylactic/therapeutic potential of CBM polypeptides as an antiviral against the influenza virus, initial studies were performed to determine the dose of CBM40 required to administer in mice. These studies were conducted at the animal testing facility for influenza research at the Centre for Infectious Disease at Edinburgh. For this, BALB/c mice, 5-6 weeks of age, were used to perform a dose finding experiment to test for adverse reactions, based on doses initially for the in vitro findings. Mice were dosed intranasally using 3CBM40 polypeptide at 50 µg in 40 µl PBS, and at 500 µg in 40 µl PBS. PBS and BSA were used as controls. The mice were monitored daily for clinical signs and weighed daily from day 2 onwards. The mice were culled on day 5 (except two of the 500 µg dosed mice, which were left for 14 days before culling).

Efficacy of CBM40 Against the Influenza A Virus

To evaluate the prophylactic and therapeutic efficacy of CBM40 against influenza A/WSN/33(H1N1), BALB/c mice were lightly anaesthetised with a Halothane Oxygen mix before treatment with 3CBM40 and virus. The CBM40 dosage for the experiment was 500 µg of 3CBM40 in PBS (40 µl), which was delivered intranasally, only once. BSA and PBS were used as the controls. Mice were treated with the CBM40 or the placebo, starting 1 day before or on the day, or +1 or +3 days after intranasal infection with $10^3$ A/WSN/33 pfu. Virus titres for each group were determined 6 days post infection where mice were culled and lungs homogenized in PBS to extract virus for plaque assays. Body weights of culled mice were also measured to determine weight loss.

Results

Structure of the Isolated CBM40 Module

Figure 3A:
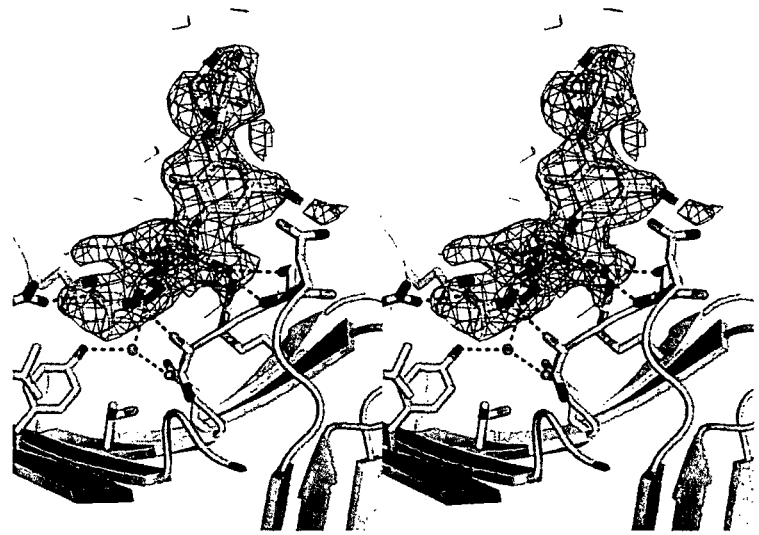
Figure 3B:
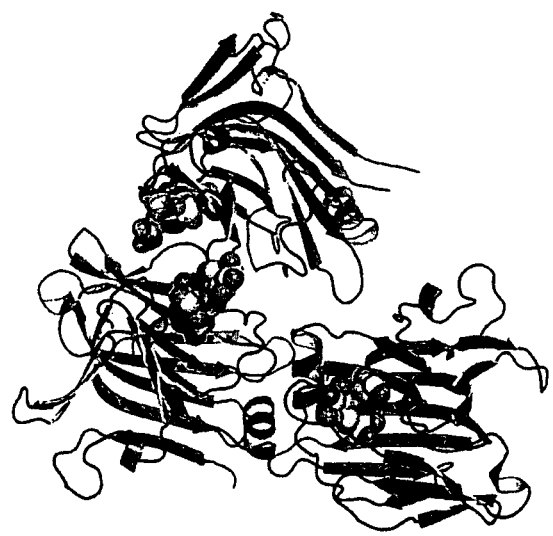

The gene fragment encoding the sialic acid binding module CBM40 from the *Vibrio cholerae* sialidase was subcloned into pEHISTEV and expressed in *E. coli* to generate 1CBM which was subsequently purified for binding and structural studies. Initially, 1CBM was expressed insolubly albeit at very high levels, but a heat shock of cultures at 42° C. during log phase of growth improved the solubility of this CBM such that up to 50-70 milligram quantities per liter were produced consistently. Crystals of *V. cholerae* CBM40 were grown in the presence of 3'sialyllactose. The asymmetric unit contained three CBM40 monomers, and each had clear electron density for all three sugar moieties of the ligand (FIG. 3A). Only sialic acid makes interactions with the protein, and these are the same as those made by sialic acid alone in complex with the whole *V. cholerae* sialidase. There are three CBM40 modules in the asymmetric unit of the crystal, with monomers A and B burying an interface of some 750 Å$^2$ (FIG. 3B).

Determination of Sialoside and Linkage Specificity of *V. cholerae* CBM40

Studies were performed with 1CBM to determine its specificity towards different mono- and divalent-sialosides. Using ITC, the binding constant $K_a$ and changes in enthalpy ($\Delta H$) and entropy ($\Delta S$) were measured directly for each interaction and stoichiometries (n, number of binding sites) were determined from nonlinear least squares fit of the data to the one-site binding model as described above. Data obtained from heat of dilution-corrected binding isotherms demonstrate the preference of 1CBM for α-sialic acids (FIG. 4), exhibiting broad binding specificity to α(2,3), α(2,6) and α(2,8)-linked sialosides. All sialosides tested displayed similar affinity with dissociation constants, $K_d$, ranging between 10-19 µM (at 25° C.) (Table 4, FIG. 4). The disialosides, DSLNT and DSL show 1.5-2 times greater affinity to sialic acid compared to monovalent ligands. DSLNT showed a large change in enthalpy, with a $\Delta H$ value of −24 kcal/mol, compared to DSL (−12.5 kcal/mol). When comparing the stoichiometries for binding DSLNT and DSL, corresponding n values of 0.57 and 0.92 were observed, indicating that for the DSLNT, two molecules of 1CBM are required to bind to 1 molecule of DSLNT, whereas for DSL there is a 1:1 interaction. The difference here is due, not just to the number of sialic acid moieties present, but to their position within the sialoside. Structurally, DSLNT is a branched divalent sialoside, unlike DSL, which has two sialic acid moieties linked together in a linear fashion, so that only the terminal sialic acid moiety is recognized (FIG. 2). This result indicates that the $\Delta H$ value of DSLNT is approximately the sum of the individual binding enthalpies of 3'sialyllactose, 6'sialyllactose and DSL, which have a stoichiometry of one.

Engineering of Multivalent, Sialic Acid-Specific CBM40 Polypeptides

We wanted to investigate whether sialic acid binding would occur if identical copies of 1CBM were linked together to produce a multivalent species. For this, copies of the gene encoding CBM40 were tethered together with a DNA linker (representing up to 15 amino acids) to create polypeptides of 2, 3 and 4 modules in tandem, which have been designated as 2CBM(5), 2CBM(10), 2CBM(15), 3CBM(5), 3CBM(10) and 4CBM(5), respectively (the figure in parenthesis indicates the number of linker amino acids) (FIG. 1B). Expression of these gene constructs was performed in *E. coli* and all demonstrated insolubility until cultures were subjected to heat shock as for the isolated 1CBM. After purification with nickel affinity chromatography, SDS PAGE analysis of all peptide constructs demonstrated monomeric molecular weights of ~21 kDa, ~42 kDa, ~63 kDa and ~85 kDa for 1CBM, 2CBM, 3CBM and 4CBM constructs, respectively (data not shown).

The binding isotherms of the various engineered CBM40 polypeptides with monovalent 3'sialyllactose are shown in FIG. 5. Using ITC, it was revealed that the binding of this sialoside to the designed CBM40 polypeptides is enthalpically driven, with $\Delta H$ values being very similar ranging from −12.3 to −16.3 kcal/mol at 25° C. (Table 5). There is also very little difference in all of the other thermodynamic parameters measured for each polypeptide interaction. In fact, the binding affinity of the multivalent CBM40s to sialic acid appeared to be similar to that of the 1CBM. Furthermore, the length of the linker between modules was not shown, thermodynamically, to contribute significantly to this interaction (Table 5). Based on the one-site binding model, the n values demonstrate the appropriate number of sites for each CBM40 polypeptide, interacting with 3'sialyllactose. The fact that no significant increase in affinity is seen as we increase the number of linked modules, suggests that the sialic acid-multivalent polypeptide interaction is similar to that of a monovalent-monomeric one, indicating a simple bimolecular association.

Enhanced Binding Affinity of Multivalent CBM40 Polypeptides for Multivalent 3' Sialyllactose In order to test whether an avidity effect for sialic acid can be achieved with multivalent CBM40 polypeptides, surface plasmon resonance (SPR) was performed using biotinylated 3'sialyllactose immobilized on a streptavidin chip. Sensorgrams for all the CBM40 polypeptides injected over immobilised 3'sialyllactose are shown in FIG. 6. The affinity for each CBM40-3'SL interaction, described here as the equilibrium dissociation constant $K_d$, was determined by a global fit model derived from the ratio of association/dissociation rate constants ($k_a/k_d$), assuming Langmuir 1:1 binding (Table 6). An increase in affinity towards sialic acid is observed as the number of modules is increased. For the 1CBM-3'SL interaction at 25° C., there is a 10-fold increase in binding ($K_d$~1.8 µM) compared to that of the corresponding monomeric-monovalent interaction ($K_d$~18 µM) measured by ITC. Enhanced affinity is observed when the number of modules increases to two, where there is an approximate 400-500-fold increase in binding, resulting in affinities between 38-45 nM at 25° C. (Table 6). The linker length appears to influence marginally the avidity in this case, as only a 1.2-fold increase in affinity is seen when increasing the number of amino acids from 5 to 15. With three and four CBM40 modules there is a further 10 to 20-fold enhancement in affinity to sialic acid, reaching affinities of around 4 nM for the 5aa-, and 10aa-linked 3CBM modules, and 2.6 nM for the 4CBM module at 25° C. The highest affinity was 4CBM(5) with a $K_d$~861 pM when binding multivalent 3'SL at 15° C. Thus, it appears that a 7000-10000-fold increase in affinity can be achieved by going from a monovalent-monomeric interaction to a multivalent one, depending on the temperature of the interaction. Data derived from van't Hoff plots for each CBM40 polypeptide-sialic acid interaction measured at 15, 25 and 35° C. (FIG. 7, Table 7), demonstrate ΔG values of −7.8 kcal/mol for 1CBM, around −10 kcal/mol for 2CBM, −11.3 kcal/mol for 3CBM and −12 kcal/mol for 4CBM. The large difference in ΔG values between 1CBM and 2CBM, is also reflected in the changes in enthalpy and entropy of the interaction. Out of all the CBM40 polypeptides, the 2CBM polypeptides gave the largest enthalpic change with a ΔH value around −20 kcal/mol, which compensated a large unfavourable entropic contribution (Table 7). This large difference in the energetics between 1CBM and 2CBM interactions is also shown in the enhanced affinity of 2CBM to sialic acid, compared to 1CBM, 3CBM and 4CBM polypeptides, suggesting cooperativety of the ligand-receptor interaction.

In contrast, the 3CBM polypeptides showed small favourable entropic gains but the change in free energy of the interaction was still strongly negative due to a better favourable enthalpic penalty (Table 7). Interestingly, both 3CBM and 4CBM polypeptides demonstrated less negative contributions to both ΔH and TΔS on ligand binding compared to 1CBM and 2CBM polypeptides, despite the fact that free energy of the interactions increased with increasing number of modules, which probably contributed to the gain in affinities. This observation could be based on a number of factors such as the interaction is sensitive to linker flexibility due to the conformational arrangement of modules, the accessibility of ligand binding sites, the modes of binding such as intra-, and intermolecular binding, and internal structural packing of the modules. The influence of linker length between the 3CBM polypeptides, however, was negligible in terms of binding energy and affinity, similar to the different 2CBM polypeptides. Since no relevant gain in affinity was achieved with 4CBM(5) at 25° C., it was decided that no further design of polypeptides would be undertaken.

Hemagglutination Assay

In order to test whether the monomeric and multivalent CBM40s bound to red blood cells and prevent binding of influenza virus, initial experiments were performed with titrated CBMs, and with the titrated virus, vaccine strain X31, against red blood cells. Preliminary results indicated that in the case of 1CBM40, no agglutination was seen, and as this CBM is monomeric, it is expected to bind in a univalent fashion to cell surface sialic acids, ie a 1:1 association (FIG. 9a). As for the multivalent CBM40s, both 2 and 3CBMs agglutinated red blood cells, as did the vaccine X31 (FIG. 9a). In addition, the end-point concentration of the multivalent CBM required to agglutinate cells, was lower for 3CBM40 than for the 2CBM (0.122 µM and 0.48 µM, respectively) suggesting that an increase in the number of repeat modules increases the binding affinity of these to sialic acid. However, since the multivalent CBMs agglutinated red blood cells, it was decided to test a mixture of titrated vaccine with a fixed concentration of 1CBM (71.25 µM) against vaccine only to observe agglutination. As seen in FIG. 9b, the presence of 1CBM when challenged with vaccine, prevents binding of the virus, when compared to mock cells (virus only). When plates were left for 2.5 days at 4° C., no agglutination was observed in the presence of 1CBM and virus, suggesting the effectiveness of this CBM40 to blocking the binding of a competing molecule.

Plaque Assay

Preliminary results of the plaque assay provide strong evidence to suggest that the 1/100 dilution of 10 mg/ml 3CBM (5) is more efficient at blocking viral entry, into cells than the same diluted concentration of 2CBM(10) (See FIG. 8). In particular, it can be seen that there is a difference in the number of plaques after incubation of MDCK cells with the different repeat CBMs, when compared to mock cells, and when 3CBM(5) is used, in the presence of H3N2, very few plaques appear.

For 3CBM(5) (1/100 dilution), there is an 80-85% reduction of H3N2 virus plaque forming units. For the 2CBM(10) result, although there is an effect on viral blocking, the same dilutions of the same concentration did not have the same effect as 3CBM(5). As such, it appears that an increase in number of CBM modules could be important in effectively blocking viral binding to sialic acid at the cell surface.

Plaque Studies (Using CBMTD)

Virus infected MDCK cells:—the influenza strain A/Udorn/72 (H3N2) virus was blocked by CBM40 polypeptides. FIG. 10 shows the cell protection effect of polypeptides 3CBM40, 4CBM40 and CBMTD on MDCK cells against the Udorn virus. There appears to be an increase in potency of CBM inhibition against the influenza strain as the number of linked CBM40s increase from 3 to 4CBM40. Also, incubation of MDCK cells with the oligomer CBM.TD, before the addition of virus, showed effective inhibition at 0.5 mg/ml and significant reduction in the number of plaques at 0.1 mg/ml CBM compared to the virus control (FIG. 10). These data demonstrate that the *V. cholerae* sialidase CBM40, whether tandem-linked or as a self-assembled oligomer, of up to 4 domain repeats, can effectively protect MDCK cells from virus infection.

Monitoring Cell-Surface Bound Sialic Acid by CBM40

Figure 11A:
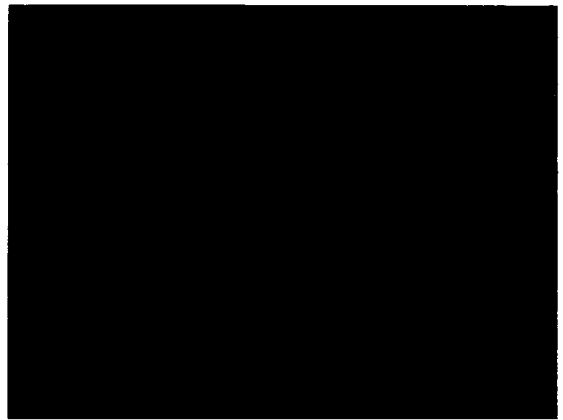
Figure 11B:
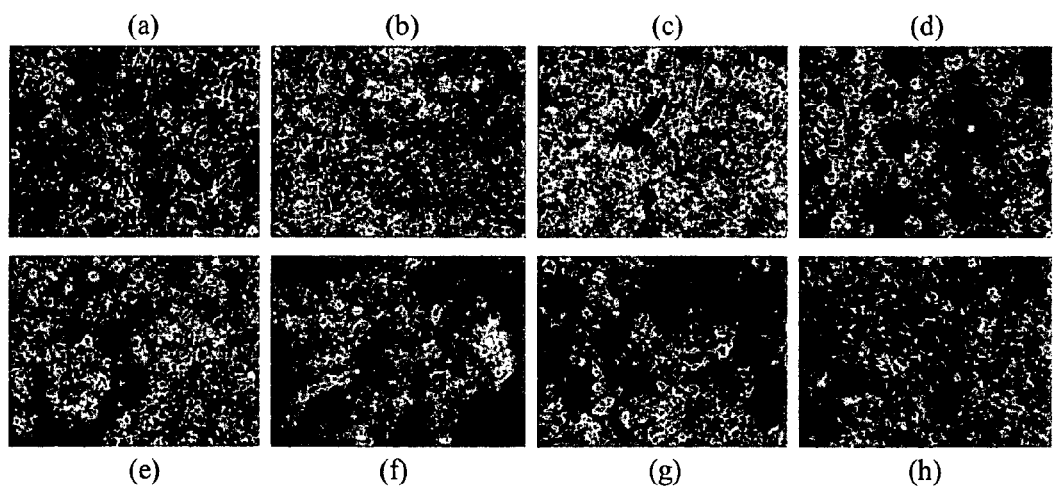

FIG. 11*a* shows the binding of GFP-3CBM40 to cell surface of MDCK cells 1 h after the addition of virus. FIG. 11*b* demonstrates that GFP-3CBM40 does confer some protection from virus infection, even after 72 h post infection when compared to the virus only well. Panel (a) also demonstrated that CBM (0.5 mg/ml) added to MDCK cells, in the absence of virus, showed no toxic effects after 72 h as cells were observed to be viable, with similar morphology to the uninfected control [panel (h)].

Mouse Studies (Dose Finding Experiment)

Table 1 shows the results of the starting and finishing weights of the mice in the study. From clinical observations, the mice all appeared to be very healthy, and that they all gained weight with no adverse effects to 3CBM40 during the specified time period of 5 days and 14 days. Further studies, in terms of antibody response and lung tissue histology, have yet to be carried out.

Efficacy of CBM40 Against Influenza A Virus

Preliminary results suggest that the administration of 3CBM40 one day before WSN virus challenge was shown to significantly reduce the effects of viral infection in mice, demonstrating that CBM40 is effective as a prophylactic against the influenza A virus. This was evident in the reduction of viral titres of mice culled on day 6 p.i., compared to the BSA and PBS controls, where only an increase of 1.5 log titres was measured from an initial dose of $10^3$ virus pfu (FIG. 12A). The mice in this group also gained weight and showed no adverse effects from the virus challenge (FIG. 12B). When 3CBM40 was administered at the same time as the virus (Day 0), a 2.4-log increase of virus was observed 6 days p.i, with weight gain being more than 100%, indicating that, despite the increase in viral titres, the mice tolerated the virus infection. However, when CBM40 was administered 1 and 3 days after virus infection, the mice appeared to lose weight and the viral titres increased by 3 to 3.25 logs compared to the initial load, suggesting that CBM40 may not be effective when given as a therapeutic, at least under the conditions described in the method. Further studies, which would include daily dosing during infection, instead of one dose, and optimization of route administration, may determine whether CBM40 could be considered as a therapeutic antiviral, particularly in the early stages of influenza infection. As a prophylactic, this protein biologic could be delivered intranasally to protect the respiratory epithelial mucosa from virus attack.

Discussion

We have shown that the sialic acid-specific CBM from *V. cholerae* sialidase can be successfully isolated from its parent enzyme and exploited to generate multivalent polypeptides that bind sialic acid with high affinity. Using a combination of ITC and SPR, we have also demonstrated thermodynamics of binding of both monovalent and multivalent forms of *V. cholerae* CBM40 to sialic acid, which appears in the mono- and divalent form to be enthalpically driven, as are many CBM-carbohydrate interactions to date (Boraston et al 2004, etc), but entropically driven when number of linked modules is greater than 2 when introduced to a multivalent surface.

With respect to its ligand and linkage specificity, the isolated CBM40 preferentially binds α(2,3), α(2,6) and α(2,8)-linked sialic acids with micromolar affinity. This binding affinity is similar to that reported for *V. cholerae* sialidase interaction with a non-hydrolysable thiosialoside (16). The fact that there is little discrimination between different linked sialosides can be seen in the crystal structure of the CBM40 complexed with 3'sialyllactose. The structure reveals an extensive network of intermolecular interactions with sialic acid. The galactose and glucose moieties do not interact with the protein domain, and this is reflected in the similar $K_d$ values and free energy of binding seen here with different linked sialosides.

By exploiting the relatively high monovalent affinity of *V. cholerae* CBM40 for sialic acid, we have successfully engineered tandem-linked repeat polypeptides up to n=4 to achieve sub-nanomolar avidity when interacting with a multivalent surface. This is possibly the first report of a CBM that has been manipulated by fusing identical copies of it using different length linker peptides. There have been previous reports of the use of isolated CBMs as molecular probes for analysis of plant cell wall polymers (21) as well as the study of CBMs naturally found in multimodular glycoside hydrolases, which have been isolated either as separate modules or as combinations with their neighbouring modules to determine their function (14,17,22).

We wanted to explore the thermodynamics of a multivalent interaction with its receptor to determine whether conformational constraints would prevent these engineered polypeptides from binding. It is well known that linker length between protein subunits can influence the thermodynamics of an interaction, and in many cases, covalently linking subunits can enhance oligomeric stability of an interaction by reducing the entropic driving force for dissociation (23). We engineered flexible peptide linkers between CBM modules ranging from 5 amino acids to 15 amino acids to determine whether linker length would significantly enhance the affinity of the engineered CBM polypeptides for sialic acid. In the case for 2-tandem linked CBMs, increasing the peptide linker to 10 amino acids gave a significant reduction in conformational entropy despite observing a 1.5-2-fold increase in affinity to sialic acid between the different 2CBM constructs. This suggests that some degree of flexibility of the modules has occurred when two CBMs are linked together. The binding interaction of 2CBMs to sialic acid also showed an increase in binding enthalpy which compensated the large unfavourable entropic contribution, resulting in an increase of free energy of binding as well as enhanced affinity for sialic acid, when compared to 1CBM-multivalent 3SL interaction. This suggests that binding of 2CBM to sialic acid is a very stable, intramolecular interaction and as for 1CBM, is enthalpically driven. However, for 3CBMs interacting with immobilised multivalent 3SL, there was no significant difference between different length peptides. In fact, entropy data derived from van't Hoff plots of the different 3CBM-sialic acid interactions all show an increase in entropy. Also, a significant decrease in binding enthalpy, and a 10-fold enhancement of affinity was observed when going from 2 to 3 CBMs. It is likely that the enhancement of affinity observed in the case of 3CBM binding to sialic acid could result from the probable formation of stable aggregates occurring at the surface of the SPR chip and that the large change in entropy could be due to structurally ordered water molecules being released from the hydration shells, influenced by tight protein-protein packing. This can be seen from the structure of the 1CBM-3SL complex, where three 1CBM monomers are closely packed together (FIG. 3B). Entropy-driven interactions have been seen in other multivalent protein-carbohydrate systems particularly where intermolecular binding occurs, leading to the formation of aggregates (24) (25), (26). Interestingly, increasing the number of linked modules to 4, demonstrated a less favourable entropic contribution to that of 3CBMs and favourable binding enthalpy although this is slightly less than that of the 1CBM interaction with immobilised 3'SL. The free energy of binding was slightly greater than all the other CBMs corresponding to a slight increase in affinity from 3 to 4CBM. It is likely that the valency of the engineered tandem-linked polypeptides may play an important part in the stabilization of oligomers and their interaction. Poon (20) describes that increasing the valency of a tandem-linked single polypeptide chain can lead to a corresponding reduction in the molecularity of a tethered oligomer which, thermodynamically speaking, becomes more stable. In practice, Poon states that a tandem of valency higher than, or not divisible by the molecularity of the oligomer will result in cross-linked oligomers. Thus for a tetrameric oligomer, such as in the case of 4CBM, a tandem dimer or tetramer would be desirable, whereas a trimeric or pentameric oligomer requires a tandem of the same respective valency.

These studies have shown that a CBM40 can be isolated and manipulated by fusing identical copies of it to enhance its affinity to sialic acid through avidity. Furthermore, we have shown that the monomer and engineered multimeric CBM40 from *V. cholerae* sialidase can be used as potential antivirals against the influenza A virus. Using this type of technology, it is therefore possible that other CBMs could be isolated and engineered for use as high affinity tools for glycan screening and profiling. In addition, determination of a CBM structure in complex with its glycan can aid in the development of selective reagents for use in the field of glycomics.

REFERENCES

1. Angata, T., and Varki, A. (2002) Chemical reviews 102(2), 439-469.
2. Lehmann, F., Tiralongo, E., and Tiralongo, J. (2006) Cell Mol Life Sci 63(12), 1331-1354.
3. Lis, H., and Sharon, N. (1998) Chem Rev 98(2), 637-674.
4. Mandal, C., and Mandal, C. (1990) Experientia 46(5), 433-441.
5. Crocker, P. R. (2002) Current Opinion in Structural Biology 12(5), 609-615.
6. Ehrhardt, C., Kneuer, C., and Bakowsky, U. (2004) Adv Drug Deliv Rev 56(4), 527-549.
7. Lee, R. T., and Lee, Y. C. (2000) Glycoconj J 17(7-9), 543-551.
8. Sacchettini, J. C., Baum, L. G., and Brewer, C. F. (2001) Biochemistry 40(10), 3009-3015.
9. Williams, D. H., O'Brien, D. P., Sandercock, A. M., and Stephens, E. (2004) J Mol Biol 340(2), 373-383.
10. Williams, D. H., Stephens, E., O'Brien, D. P., and Zhou, M. (2004) Angew Chem Int Ed Engl 43(48), 6596-6616.
11. Williams, D. H., Stephens, E., and Zhou, M. (2003) J Mol Biol 329(2), 389-399.
12. Mathai Mammen, S.-K. C., George M. Whitesides (1998) Angewandte Chemie International Edition 37(20), 2754-2794.
13. Boraston, A. B., Bolam, D. N., Gilbert, H. J., and Davies, G. J. (2004) Biochem J 382(Pt 3), 769-781.
14. Boraston, A. B., McLean, B. W., Chen, G., Li, A., Warren, R. A., and Kilburn, D. G. (2002) Mol Microbiol 43(1), 187-194.
15. Crennell, S., Garman, E., Laver, G., Vimr, E., and Taylor, G. (1994) Structure 2(6), 535-544.
16. Moustafa, I., Connaris, H., Taylor, M., Zaitsev, V., Wilson, J. C., Kiefel, M. J., von Itzstein, M., and Taylor, G. (2004) J Biol Chem 279(39), 40819-40826.
17. Boraston, A. B., Ficko-Blean, E., and Healey, M. (2007) Biochemistry 46(40), 11352-11360.
18. McCoy, A., Grosse-Kunstleve, R. W., Adams, P., Winn, M., Storoni, L., and Read, R. (2007) J. Appl. Cryst. 40, 658-674.
19. Murshudov, G., Vagin, A., and Dodson, E. (1997) Acta. Cryst. D53, 240-255
20. Emsley, P., and Cowtan, K. (2004) Acta Crystallogr D Biol Crystallogr 60(Pt 12 Pt 1), 2126-2132.
21. McCartney, L., Gilbert, H. J., Bolam, D. N., Boraston, A. B., and Knox, J. P. (2004) Anal Biochem 326(1), 49-54.
22. Guillen, D., Santiago, M., Linares, L., Perez, R., Morlon, J., Ruiz, B., Sanchez, S., and Rodriguez-Sanoja, R. (2007) Applied and environmental microbiology 73(12), 3833-3837.
23. Poon, G. M. (2007) Biochemical Society transactions 35(Pt 6), 1574-1578.
24. Lundquist, J. J., and Toone, E. J. (2002) Chem Rev 102(2), 555-578.
25. Ambrosi, M., Cameron, N. R., Davis, B. G., and Stolnik, S. (2005) Organic & biomolecular chemistry 3(8), 1476-1480.
26. Vyas, N. K., Vyas, M. N., Chervenak, M. C., Johnson, M. A., Pinto, B. M., Bundle, D. R., and Quiocho, F. A. (2002) Biochemistry 41(46), 13575-13586.
27. Xu, G., Ryan, C., Kiefel, M. J., Wilson, J. C. and Taylor, G. L. (2009) J. Mol. Biol. 386(3), 828-840.
28. Liu, H., and Naismith, J. H. (2009) *Protein Expr Purif* 63, 102-111.
29. Connaris, H., Crocker, P., and Taylor, G. L. (2009) J. Biol. Chem., 284(11) 7339-7351.

TABLE 1

Dose finding experiment of 3CBM40 administered in BALB/c mice.

| Mouse number | Cage/group | Dose | Weight day 0 | End weight |
|---|---|---|---|---|
| 89 | 5 dys | 50 ug 3CBM | 17.1 | 17.5 |
| 90 | 5 dys | 50 ug 3CBM | 15.05 | 15.5 |
| 91 | 5 dys | PBS | 12.5 | 13.1 |
| 92 | 5 dys | PBS | 14.7 | 15.4 |
| 93 | 5 dys | 500 ug 3CBM | 15.45 | 16.70 |
| 94 | 14 dys | 500 ug 3CBM | 14.6 | 18.3 |
| 95 | 14 dys | 500 ug 3CBM | 14 | 18.1 |
| 96 | 5 dys | 500 ug 3CBM | 14.75 | 16.05 |
| 97 | 5 dys | 500 ug BSA | 14.8 | 15.4 |
| 98 | 5 dys | 500 ug BSA | 13.4 | 14 |
| 99 | | Tkip | 16.4 | 16.60 |
| 100 | | Tkip | 16.05 | 17.2 |
| 101 | | Tkip | 16.45 | 18.6 |
| 102 | | Tkip | 15 | 18.1 |
| 103 | | 0.5% DMSO | 17.15 | 18.25 |
| 104 | | 0.5% DMSO | 14.85 | 16.8 |

TABLE 2

Oligonucleotide primers used to amplify DNA fragments.

| Primer | Oligonucleotide sequence |
|---|---|
| 1F | CGTCCCATGGCACTTTTTGACTATAACGC(NcoI) (SEQ ID NO: 1) |
| 1R | CCGGCTCGAGCTAGTCGCCTTGAATTTCAA AC(XhoI) (SEQ ID NO: 2) |
| 2F (5) | CGTCGGATCCATGGCACTTTTTGAC(BamHI) (SEQ ID NO: 3) |

TABLE 2-continued

Oligonucleotide primers used to amplify DNA fragments.

| Primer | Oligonucleotide sequence |
|---|---|
| 2R (5) | GCACGGATCCGTTCAGGGCGTCGCCTTGAAT TT(BamHI) (SEQ ID NO: 4) |
| 2F (10) | GCCTGGATCCGGTATGGCACTTTTTGACTAT AAC(BamHI) (SEQ ID NO: 5) |
| 2R (10) | GACCGGATCCACCTCCTGATCCGTTCAGGGCGTCG CC(BamHI) (SEQ ID NO: 6) |
| 2R (15) | GACCGGATCCACCTCCACCTGATCCACCTCCTGAT CC(BamHI) (SEQ ID NO: 7) |
| 3F (5) | CTGCAAGCTTTGGGAATGGCACTTTTTG AC(HindIII) (SEQ ID NO: 8) |
| 3R (5) | GCACTTCCAAAGCTTGCAGGTCGCCTTGAATTT C(HindIII) (SEQ ID NO: 9) |
| 3F (10) | GGTGGAAGCTTGATGGCACTTTTTGACTATA AC(HindIII) (SEQ ID NO: 10) |
| 3R (10) | GTCCAAGCTTCCACCTCCTCCCAATGCTTGCAGGTCG CC(HindIII) (SEQ ID NO: 11) |
| 4F (5) | GGTAGGGAATTCGGGAATGGCACTTTTTGACTATA AC(EcoRI) (SEQ ID NO: 12) |
| 4R (5) | GCACTCCCGAATTCCCTCCGTCGCCTTGAAT TTC(EcoRI) (SEQ ID NO: 13) |

TABLE 3

X-ray data collection and refinement statistics. Numbers in parentheses refer to the highest resolution shell.

| Data collection | |
|---|---|
| Space group | $C222_1$ |
| Unit cell edges (Å) | a = 138.6, b = 197.6, c = 83.0 |
| X-ray source | ESRF BM-14 |
| Resolution range | 30-2.5 Å |
| Completeness (%) | 95.4 (88.6) |
| $R_{merge}$ | 0.064 (0.414) |
| $<I/\sigma I>$ | 15.8 (2.7) |
| Refinement | |
| No. of reflections work/test | 35,893/1,911 |
| $R_{cryst}$ | 0.224 |
| $R_{free}$ | 0.263 |
| r.m.s.d. bond distance (Å) | 0.017 |
| r.m.s.d bond angle (°) | 1.716 |

$R_{merge} = \Sigma_{hkl}\Sigma_i |I_{hkl,i} - <I_{hkl}>|/\Sigma_{hkl}<I_{hkl}>$
$R_{cryst}$ and $R_{free} = (\Sigma ||F_o| - |F_c||)/(\Sigma |F_o|)$

TABLE 4

Thermodynamic parameters of interaction of isolated CBM40 from *V. cholerae* sialidase with different linkage sialosides.

| Sialoside | Linkage specificity | n | ΔH (kcal/mol) | TΔS (kcal/mol) | ΔG (kcal/mol) | $K_a$ ($10^{-4}$M) | $K_d$ (μM) |
|---|---|---|---|---|---|---|---|
| 3'SL | α2, 3 | 0.96 ± 0.002 | −16.3 ± 0.05 | −9.8 | −6.5 | 5.48 ± 0.05 | 18 |
| 6'SL | α2, 6 | 1.02 ± 0.001 | −9.9 ± 0.002 | −3.5 | −6.4 | 5.16 ± 0.03 | 19 |
| DSL | α2, 8 α2, 3 | 0.92 ± 0.001 | −12.5 ± 0.003 | −5.7 | −6.8 | 10.2 ± 0.01 | 9.8 |
| DSLNT | α2, 6, α2, 3 | 0.57 ± 0.001 | −24.0 ± 0.007 | −17.3 | −6.7 | 7.8 ± 0.06 | 13 |

TABLE 5

ITC results of binding of CBM40 peptides to 3'sialyllactose (duplicate measurements).

| Peptide | [P] mM | [3'SL] mM | n | ΔH (kcal/mol) | TΔS (kcal/mol) | ΔG (kcal/mol) | $K_a$ ($10^{-4}$M) | $K_d$ (μM) |
|---|---|---|---|---|---|---|---|---|
| 1CBM | 0.084 | 1.04 | 0.96 ± 0.002 | −16.3 ± 0.05 | −9.8 | −6.5 | 5.48 ± 0.05 | 18 |
| 2CBM(5) | 0.071 | 2.19 | 2.00 ± 0.003 | −12.3 ± 0.03 | −6.2 | −6.1 | 3.18 ± 0.02 | 31 |
| 2CBM(10) | 0.033 | 1.14 | 1.93 ± 0.007 | −13.7 ± 0.07 | −7.3 | −6.4 | 4.36 ± 0.05 | 22 |
| 2CBM(15) | 0.026 | 0.79 | 1.99 ± 0.014 | −13.8 ± 0.01 | −7.5 | −6.3 | 3.49 ± 0.04 | 28 |
| 3CBM(5) | 0.018 | 0.75 | 2.96 ± 0.003 | −13.5 ± 0.03 | −7.2 | −6.3 | 3.63 ± 0.04 | 27 |
| 3CBM(10) | 0.016 | 0.72 | 3.09 ± 0.024 | −13.5 ± 0.01 | −7.1 | −6.4 | 4.54 ± 0.09 | 22 |
| 4CBM(5) | 0.007 | 0.45 | 3.96 ± 0.322 | −15.8 ± 0.02 | −9.6 | −6.2 | 3.56 ± 0.03 | 28 |

TABLE 6

Biacore kinetic parameters for the different CBM polypeptides interacting with multivalent 3'sialyllactose (n = 3 determinations).

| Peptide | T | $k_a$ (M$^{-1}$s$^{-1}$) | $k_d$ (s$^{-1}$) | $K_D$ (M) |
|---|---|---|---|---|
| 1CBM | 35 | $(3.1 \pm 0.05) \times 10^3$ | $(1.8 \pm 0.3) \times 10^{-2}$ | $5.8 \times 10^{-6}$ |
|  | 25 | $(4.3 \pm 0.7) \times 10^3$ | $(7.6 \pm 0.4) \times 10^{-3}$ | $1.8 \times 10^{-6}$ |
|  | 15 | $(3.7 \pm 0.4) \times 10^3$ | $(3.6 \pm 0.9) \times 10^{-3}$ | $9.7 \times 10^{-7}$ |
| 2CBM(5) | 35 | $(3.5 \pm 0.2) \times 10^5$ | $(3.6 \pm 0.04) \times 10^{-2}$ | $1.0 \times 10^{-7}$ |
|  | 25 | $(5.6 \pm 0.7) \times 10^5$ | $(2.5 \pm 0.1) \times 10^{-2}$ | $4.5 \times 10^{-8}$ |
|  | 15 | $(7.4 \pm 0.13) \times 10^5$ | $(9.5 \pm 0.07) \times 10^{-3}$ | $1.3 \times 10^{-8}$ |
| 2CBM(10) | 35 | $(2.0 \pm 0.1) \times 10^4$ | $(2.6 \pm 0.2) \times 10^{-3}$ | $1.3 \times 10^{-7}$ |
|  | 25 | $(5.9 \pm 0.3) \times 10^5$ | $(2.3 \pm 0.23) \times 10^{-2}$ | $3.9 \times 10^{-8}$ |
|  | 15 | $(8.1 \pm 0.17) \times 10^5$ | $(6.9 \pm 0.05) \times 10^{-3}$ | $8.5 \times 10^{-9}$ |
| 2CBM(15) | 35 | $(5.3 \pm 0.6) \times 10^5$ | $(5.2 \pm 0.3) \times 10^{-2}$ | $9.8 \times 10^{-8}$ |
|  | 25 | $(8.8 \pm 0.5) \times 10^5$ | $(3.4 \pm 0.08) \times 10^{-2}$ | $3.8 \times 10^{-8}$ |
|  | 15 | $(8.7 \pm 0.5) \times 10^5$ | $(8.7 \pm 0.3) \times 10^{-3}$ | $1 \times 10^{-8}$ |
| 3CBM(5) | 35 | $(5.2 \pm 0.35) \times 10^5$ | $(4.4 \pm 0.2) \times 10^{-3}$ | $8.44 \times 10^{-9}$ |
|  | 25 | $(5.6 \pm 0.15) \times 10^5$ | $(2.3 \pm 0.08) \times 10^{-3}$ | $4.0 \times 10^{-9}$ |
|  | 15 | $(3.0 \pm 0.3) \times 10^5$ | $(1.1 \pm 0.04) \times 10^{-3}$ | $3.7 \times 10^{-9}$ |
| 3CBM(10) | 35 | $(5.1 \pm 0.01) \times 10^5$ | $(4.1 \pm 0.48) \times 10^{-3}$ | $8.07 \times 10^{-9}$ |
|  | 25 | $(4.5 \pm 0.4) \times 10^5$ | $(1.95 \pm 0.03) \times 10^{-3}$ | $4.26 \times 10^{-9}$ |
|  | 15 | $(3.3 \pm 0.2) \times 10^5$ | $(1.21 \pm 0.02) \times 10^{-3}$ | $3.63 \times 10^{-9}$ |
| 4CBM(5) | 35 | $(2.2 \pm 0.8) \times 10^5$ | $(9.2 \pm 0.07) \times 10^{-4}$ | $4.01 \times 10^{-9}$ |
|  | 25 | $(2.8 \pm 0.5) \times 10^5$ | $(7.4 \pm 0.9) \times 10^{-4}$ | $2.62 \times 10^{-9}$ |
|  | 15 | $(2.9 \pm 0.4) \times 10^5$ | $(2.5 \pm 0.01) \times 10^{-4}$ | $8.61 \times 10^{-10}$ |

TABLE 7

Thermodynamic parameters for the interaction of designed sialic acid binding peptide modules with multivalent 3'sialyllactose-PAA-biotin derived from van't Hoff plots.

|  | ΔG (kcal/mol) | ΔH (kcal/mol) | ΔS (cal/mol) | TΔS (kcal/mol) |
|---|---|---|---|---|
| 1CBM | −7.8 | −15.9 | −27.3 | −8.1 |
| 2CBM(5) | −10.0 | −18.8 | −29.4 | −8.8 |
| 2CBM(10) | −10.3 | −22.4 | −40.8 | −12.1 |
| 2CBM(15) | −10.1 | −20.7 | −35.4 | −10.6 |
| 3CBM(5) | −11.3 | −7.2 | 13.8 | 4.1 |
| 3CBM(10) | −11.3 | −7.1 | 14.2 | 4.2 |
| 4CBM(5) | −11.9 | −14.1 | −7.5 | −2.2 |

The invention claimed is:

1. A method of treating or preventing a disease caused or contributed to by a pathogen, said method comprising the step of administering a therapeutically effective amount of a carbohydrate binding module (CBM) to a subject in need thereof, wherein the CBM comprises one or more isolated family 40 CBMs (CBM40).

2. The method of claim 1, wherein the disease is caused by one or more viral respiratory pathogens and/or one or more bacterial pathogens.

3. The method of claim 2, wherein the viral respiratory pathogen belongs to the Orthomyxoviridae or Paramyxoviridae families.

4. The method of claim 2, wherein the bacterial pathogen is of the *Streptococcus* genus, *Haemophilus influenzae* or *Pseudomonas aeruginosa*.

5. The method of claim 1, wherein the disease caused or contributed to by a pathogen is influenza, croup, pneumonia and/or bronchitis.

6. The method of claim 1, wherein the CBM40 exhibits an affinity for, or binds to, sialic acid.

7. The method of claim 1, wherein the CBM40 is derived from *Vibrio cholerae* or *Clostridium perfringens*.

8. The method of claim 1, wherein the CBM is a multivalent CBM comprising two or more CBM40 monomers.

9. The method of claim 1, wherein the CBM40 is modified to include a moiety to be delivered to a cell.

10. The method of claim 8, wherein the multivalent CBM comprises two or more CBM40 monomers derived from *Vibrio cholera* or *Clostridium perfringens*.

11. A method of treating or preventing disease caused or contributed to by a pathogen, said method comprising the step of administering a therapeutically effective amount of a carbohydrate binding module (CBM) to a subject in need thereof, wherein the CBM is a CBM polymer comprising two or more CBM40 monomers.

12. The method of claim 11, wherein the CBM polymer comprises two or more CBM40 monomers derived from *Vibrio cholera* or *Clostridium perfringens*.

13. A method of treating or preventing a disease caused or contributed to by a pathogen, said method comprising administering a pharmaceutical composition comprising a therapeutically effective amount of a carbohydrate binding module (CBM) and a pharmaceutically acceptable excipient to a subject in need thereof, wherein the CBM comprises one or more isolated family 40 CBMs (CBM40).

14. The method of claim 13, wherein the disease is caused by one or more viral respiratory pathogens and/or one or more bacterial pathogens.

15. The method of claim 14, wherein the viral respiratory pathogen belongs to the Orthomyxoviridae or Paramyxoviridae families.

16. The method of claim 14, wherein the bacterial pathogen is of the *Streptococcus* genus, *Haemophilus influenzae* or *Pseudomonas aeruginosa*.

17. The method of claim 13, wherein the disease caused or contributed to by a pathogen is influenza, croup, pneumonia and/or bronchitis.

18. The method of claim 13, wherein the CBM40 exhibits an affinity for, or binds to, sialic acid.

19. The method of claim 13, wherein the CBM40 is derived from *Vibrio cholerae* or *Clostridium perfringens*.

20. A method of treating or preventing a disease caused or contributed to by a pathogen, said method comprising administering a pharmaceutical composition comprising a therapeutically effective amount of a carbohydrate binding module (CBM) and a pharmaceutically acceptable excipient to a subject in need thereof, wherein the CBM is a multivalent CBM comprising two or more CBM40 monomers.

21. The method of claim 13, wherein the CBM40 is modified to include a moiety to be delivered to a cell.

22. The method of claim 20, wherein the multivalent CBM comprises two or more CBM40 monomers derived from *Vibrio cholera* or *Clostridium perfringens*.

23. The method of claim 13, wherein the CBM is a CBM polymer comprising two or more CBM40 monomers.

24. The method of claim 23, wherein the CBM polymer comprises two or more CBM40 monomers derived from *Vibrio cholera* or *Clostridium perfringens*.

25. The method of claim 1, wherein the pathogen exploits the presence of a cell surface carbohydrate as a means of binding/adhering to and/or entering a cell.

26. The method of claim 13, wherein the pathogen exploits the presence of a cell surface carbohydrate as a means of binding/adhering to and/or entering a cell.

27. The method of claim 11, wherein the disease is caused by one or more viral respiratory pathogens and/or one or more bacterial pathogens.

28. The method of claim 27, wherein the viral respiratory pathogen belongs to the Orthomyxoviridae or Paramyxoviridae families.

29. The method of claim 27, wherein the bacterial pathogen is of the *Streptococcus* genus, *Haemophilus influenzae* or *Pseudomonas aeruginosa*.

30. The method of claim 11, wherein the disease caused or contributed to by a pathogen is influenza, croup, pneumonia and/or bronchitis.

31. The method of claim 11, wherein the CBM40 exhibits an affinity for, or binds to, sialic acid.

32. The method of claim 11, wherein the CBM40 is modified to include a moiety to be delivered to a cell.

33. The method of claim 5 comprising administering a therapeutically effective amount of a CBM40 monomer.

34. The method of claim 5, wherein the disease caused or contributed to by a pathogen is influenza.

35. The method of claim 34 comprising administering a therapeutically effective amount of a CBM40 monomer.

36. The method of claim 20, wherein the CBM polymer comprises two CBM40 monomers and the disease caused or contributed to by a pathogen is influenza.

37. The method of claim 20, wherein the CBM polymer comprises three CBM40 monomers and the disease caused or contributed to by a pathogen is influenza.

38. The method of claim 20, wherein the CBM polymer comprises four CBM40 monomers and the disease caused or contributed to by a pathogen is influenza.

39. The method of claim 17, wherein the disease caused or contributed to by a pathogen is influenza.

40. The method of claim 39 comprising administering a therapeutically effective amount of a CBM40 monomer.

41. The method of claim 20, wherein the disease caused or contributed to by a pathogen is influenza, croup, pneumonia and/or bronchitis.

42. The method of claim 41, wherein the multivalent CBM comprises two CBM40 monomers and the disease caused or contributed to by a pathogen is influenza.

43. The method of claim 41, wherein the multivalent CBM comprises three CBM40 monomers and the disease caused or contributed to by a pathogen is influenza.

44. The method of claim 41, wherein the multivalent CBM comprises four CBM40 monomers and the disease caused or contributed to by a pathogen is influenza.

* * * * *

SEQUENCE LISTING

```
<160> NUMBER OF SEQ ID NOS: 19

<210> SEQ ID NO 1
<211> LENGTH: 29
<212> TYPE: DNA
<213> ORGANISM: Artificial Sequence
<220> FEATURE:
<223> OTHER INFORMATION: Primer pair 1F and 1R

<400> SEQUENCE: 1
cgtcccatgg cacttttttga ctataacgc                                    29

<210> SEQ ID NO 2
<211> LENGTH: 32
<212> TYPE: DNA
<213> ORGANISM: Artificial Sequence
<220> FEATURE:
<223> OTHER INFORMATION: Primer pair 1F and 1R

<400> SEQUENCE: 2
ccggctcgag ctagtcgcct tgaatttcaa ac                                 32

<210> SEQ ID NO 3
<211> LENGTH: 25
<212> TYPE: DNA
<213> ORGANISM: Artificial Sequence
<220> FEATURE:
<223> OTHER INFORMATION: Primer pair 1F and 1R

<400> SEQUENCE: 3
cgtcggatcc atggcacttt tgac                                          25

<210> SEQ ID NO 4
<211> LENGTH: 32
<212> TYPE: DNA
<213> ORGANISM: Artificial Sequence
<220> FEATURE:
<223> OTHER INFORMATION: Primer pair 1F and 1R
```

<400> SEQUENCE: 4
gcacggatcc gttcagggcg tcgccttgaa tt					32

<210> SEQ ID NO 5
<211> LENGTH: 34
<212> TYPE: DNA
<213> ORGANISM: Artificial Sequence
<220> FEATURE:
<223> OTHER INFORMATION: Primer pair 1F and 1R

<400> SEQUENCE: 5
gcctggatcc ggtatggcac tttttgacta taac					34

<210> SEQ ID NO 6
<211> LENGTH: 37
<212> TYPE: DNA
<213> ORGANISM: Artificial Sequence
<220> FEATURE:
<223> OTHER INFORMATION: Primer pair 1F and 1R

<400> SEQUENCE: 6
gaccggatcc acctcctgat ccgttcaggg cgtcgcc					37

<210> SEQ ID NO 7
<211> LENGTH: 37
<212> TYPE: DNA
<213> ORGANISM: Artificial Sequence
<220> FEATURE:
<223> OTHER INFORMATION: Primer pair 1F and 1R

<400> SEQUENCE: 7
gaccggatcc acctccacct gatccacctc ctgatcc					37

<210> SEQ ID NO 8
<211> LENGTH: 30
<212> TYPE: DNA
<213> ORGANISM: Artificial Sequence
<220> FEATURE:
<223> OTHER INFORMATION: Primer pair 1F and 1R

<400> SEQUENCE: 8
ctgcaagctt tgggaatggc actttttgac					30

<210> SEQ ID NO 9
<211> LENGTH: 34
<212> TYPE: DNA
<213> ORGANISM: Artificial Sequence
<220> FEATURE:
<223> OTHER INFORMATION: Primer pair 1F and 1R

<400> SEQUENCE: 9
gcacttccaa agcttgcagg tcgccttgaa tttc					34

<210> SEQ ID NO 10
<211> LENGTH: 33
<212> TYPE: DNA
<213> ORGANISM: Artificial Sequence
<220> FEATURE:
<223> OTHER INFORMATION: Primer pair 1F and 1R

<400> SEQUENCE: 10
ggtggaagct tgatggcact ttttgactat aac					33

<210> SEQ ID NO 11
<211> LENGTH: 39

<210> SEQ ID NO 11
<211> LENGTH: 39
<212> TYPE: DNA
<213> ORGANISM: Artificial Sequence
<220> FEATURE:
<223> OTHER INFORMATION: Primer pair 1F and 1R

<400> SEQUENCE: 11
gtccaagctt ccacctcctc ccaatgcttg caggtcgcc                                    39

<210> SEQ ID NO 12
<211> LENGTH: 37
<212> TYPE: DNA
<213> ORGANISM: Artificial Sequence
<220> FEATURE:
<223> OTHER INFORMATION: Primer pair 1F and 1R

<400> SEQUENCE: 12
ggtagggaat tcgggaatgg cactttttga ctataac                                      37

<210> SEQ ID NO 13
<211> LENGTH: 34
<212> TYPE: DNA
<213> ORGANISM: Artificial Sequence
<220> FEATURE:
<223> OTHER INFORMATION: Primer pair 1F and 1R

<400> SEQUENCE: 13
gcactcccga attccctccg tcgccttgaa tttc                                         34

<210> SEQ ID NO 14
<211> LENGTH: 5
<212> TYPE: PRT
<213> ORGANISM: Artificial Sequence
<220> FEATURE:
<223> OTHER INFORMATION: Linker

<400> SEQUENCE: 14

Ala Leu Asn Gly Ser
1               5

<210> SEQ ID NO 15
<211> LENGTH: 10
<212> TYPE: PRT
<213> ORGANISM: Artificial Sequence
<220> FEATURE:
<223> OTHER INFORMATION: Linker

<400> SEQUENCE: 15

Ala Leu Asn Gly Ser Gly Gly Gly Ser Gly
1               5                   10

<210> SEQ ID NO 16
<211> LENGTH: 15
<212> TYPE: PRT
<213> ORGANISM: Artificial Sequence
<220> FEATURE:
<223> OTHER INFORMATION: Linker

<400> SEQUENCE: 16

Ala Leu Asn Gly Ser Gly Gly Gly Ser Gly Gly Gly Ser Gly
1               5                   10                  15

<210> SEQ ID NO 17
<211> LENGTH: 5
<212> TYPE: PRT
<213> ORGANISM: Artificial Sequence
<220> FEATURE:
<223> OTHER INFORMATION: Linker

```
<400> SEQUENCE: 17

Leu Gln Ala Leu Gly
1               5

<210> SEQ ID NO 18
<211> LENGTH: 10
<212> TYPE: PRT
<213> ORGANISM: Artificial Sequence
<220> FEATURE:
<223> OTHER INFORMATION: Linker

<400> SEQUENCE: 18

Leu Gln Ala Leu Gly Gly Gly Gly Ser Leu
1               5                   10

<210> SEQ ID NO 19
<211> LENGTH: 5
<212> TYPE: PRT
<213> ORGANISM: Artificial Sequence
<220> FEATURE:
<223> OTHER INFORMATION: Linker

<400> SEQUENCE: 19

Gly Gly Asn Ser Gly
1               5
```